US008563707B2

(12) United States Patent
Carlson et al.

(10) Patent No.: US 8,563,707 B2
(45) Date of Patent: Oct. 22, 2013

(54) COMPOSITIONS AND METHODS FOR DETECTION OF HEPATITIS A VIRUS NUCLEIC ACID

(75) Inventors: James D. Carlson, San Diego, CA (US); Steven T. Brentano, Santee, CA (US)

(73) Assignee: Gen-Probe Incorporated, San Diego, CA (US)

( * ) Notice: Subject to any disclaimer, the term of this patent is extended or adjusted under 35 U.S.C. 154(b) by 0 days.

(21) Appl. No.: 13/243,243

(22) Filed: Sep. 23, 2011

(65) Prior Publication Data

US 2012/0015348 A1 Jan. 19, 2012

Related U.S. Application Data

(60) Continuation of application No. 12/429,589, filed on Apr. 24, 2009, now Pat. No. 8,063,197, which is a division of application No. 11/182,177, filed on Jul. 13, 2005, now Pat. No. 7,544,792.

(60) Provisional application No. 60/587,734, filed on Jul. 13, 2004.

(51) Int. Cl.

| | |
|---|---|
| ***C07H 21/04*** | (2006.01) |
| ***C12Q 1/68*** | (2006.01) |
| *A61K 39/29* | (2006.01) |

(52) U.S. Cl.

USPC .......................... 536/24.32; 435/6; 424/226.1

(58) Field of Classification Search

None

See application file for complete search history.

(56) References Cited

U.S. PATENT DOCUMENTS

| | | | |
|---|---|---|---|
| 4,581,333 | A | 4/1986 | Kourilsky et al. |
| 4,683,195 | A | 7/1987 | Mullis et al. |
| 4,786,600 | A | 11/1988 | Kramer et al. |
| 4,800,159 | A | 1/1989 | Mullis et al. |
| 4,868,105 | A | 9/1989 | Urdea et al. |
| 5,130,238 | A | 7/1992 | Malek et al. |
| 5,185,439 | A | 2/1993 | Arnold, Jr. et al. |
| 5,290,677 | A | 3/1994 | Robertson et al. |
| 5,399,491 | A | 3/1995 | Kacian et al. |
| 5,422,252 | A | 6/1995 | Walker et al. |
| 5,427,930 | A | 6/1995 | Birkenmeryer et al. |
| 5,430,135 | A | 7/1995 | Nainan et al. |
| 5,437,990 | A | 8/1995 | Burg et al. |
| 5,476,658 | A | 12/1995 | Tsarev et al. |
| 5,494,810 | A | 2/1996 | Barany et al. |
| 5,516,630 | A | 5/1996 | Ticehurst et al. |
| 5,547,842 | A | 8/1996 | Hogan et al. |
| 5,554,516 | A | 9/1996 | Kacian et al. |
| 5,656,207 | A | 8/1997 | Woodhead et al. |
| 5,656,744 | A | 8/1997 | Arnold, Jr. et al. |
| 5,658,737 | A | 8/1997 | Nelson et al. |
| 5,702,891 | A | 12/1997 | Kolberg et al. |
| 5,731,148 | A | 3/1998 | Becker et al. |
| 5,766,906 | A | 6/1998 | Lemon et al. |
| 5,786,183 | A | 7/1998 | Ryder et al. |
| 5,789,153 | A | 8/1998 | Falkner et al. |
| 5,849,562 | A | 12/1998 | Purcell et al. |
| 5,958,677 | A | 9/1999 | Lee et al. |
| 6,110,678 | A | 8/2000 | Weisburg et al. |
| 6,113,912 | A | 9/2000 | Funkhauser et al. |
| 6,136,322 | A | 10/2000 | Lemon et al. |
| 6,180,110 | B1 | 1/2001 | Funkhouser et al. |
| 6,280,952 | B1 | 8/2001 | Weisburg et al. |
| 6,361,945 | B1 | 3/2002 | Becker et al. |
| 6,423,318 | B1 | 7/2002 | Funkhouser et al. |
| 6,440,718 | B1 | 8/2002 | Probst |
| RE37,891 | E | 10/2002 | Collins et al. |
| 6,670,116 | B2 | 12/2003 | Zimmermann et al. |
| 6,942,965 | B2 | 9/2005 | Pichuantes et al. |
| 2003/0124517 | A1 | 7/2003 | Pichuantes et al. |
| 2004/0072150 | A1 | 4/2004 | Shyamala |
| 2004/0170954 | A1 | 9/2004 | McKenney et al. |
| 2004/0191794 | A1 | 9/2004 | Weindel et al. |
| 2006/0257851 | A1 | 11/2006 | Bentwich |
| 2007/0042350 | A1 | 2/2007 | Li et al. |
| 2007/0042381 | A1 | 2/2007 | Bentwich et al. |
| 2008/0311556 | A1 | 12/2008 | Iversen |
| 2008/0318210 | A1 | 12/2008 | Bentwich |
| 2012/0009565 | A1 | 1/2012 | Carlson et al. |

FOREIGN PATENT DOCUMENTS

| | | | |
|---|---|---|---|
| EP | 0199480 | A2 | 10/1986 |
| EP | 0302801 | A1 | 2/1989 |
| EP | 0714988 | A2 | 6/1996 |
| EP | 1609874 | A2 | 12/2005 |
| EP | 1818416 | A2 | 8/2008 |
| JP | 2008079576 | A | 4/2008 |
| KR | 20020078708 | A | 10/2002 |
| WO | 85/01517 | A1 | 4/1985 |
| WO | 88/00973 | A1 | 2/1988 |
| WO | 88/10315 | A1 | 12/1988 |
| WO | 91/11534 | A1 | 8/1991 |
| WO | 9601615 | A2 | 1/1996 |

(Continued)

OTHER PUBLICATIONS

USPTO Office Action, U.S. Appl. No. 12/429,589, filed Feb. 7, 2011.

USPTO Notice of Allowance, U.S. Appl. No. 12/429,589, filed Sep. 16, 2011.

EPO Proceeding Pursuant to Rule 70(2) EPC, European Patent Application No. 05 800 781.6, Feb. 19, 2009.

EPO Communication under Rule 71(3) EPC, European Patent Application No. 05 800 781.6, Apr. 17, 2012.

EPO Partial European Search Report, European Patent Application No. 11 176 256.3, Dec. 23, 2011.

EPO Extended European Search Report, European Patent Application No. 11 176 256.3, May 3, 2012.

(Continued)

*Primary Examiner* — Bao Li

(74) *Attorney, Agent, or Firm* — Jeffrey E. Landes

(57) ABSTRACT

Nucleic acid oligomeric sequences and in vitro nucleic acid amplification and detection methods for detecting the presence of HAV RNA sequences in samples are disclosed. Kits comprising nucleic acid oligomers for amplifying and detecting HAV nucleic acid sequences are disclosed.

20 Claims, No Drawings

(56) References Cited

FOREIGN PATENT DOCUMENTS

| | | | | |
|---|---|---|---|---|
| WO | WO9932633 | A1 | * | 4/1999 |
| WO | 01/14593 | A2 | | 3/2001 |
| WO | 0168921 | A2 | | 9/2001 |
| WO | 03/020742 | A1 | | 3/2003 |
| WO | 03/030624 | A2 | | 4/2003 |
| WO | 03030624 | A2 | | 4/2003 |
| WO | 03/106641 | A2 | | 12/2003 |
| WO | 03106641 | A2 | | 12/2003 |
| WO | 2004048511 | A2 | | 6/2004 |
| WO | 2005005658 | A1 | | 1/2005 |
| WO | 2005013905 | A2 | | 2/2005 |
| WO | 2005071401 | A2 | | 8/2005 |
| WO | 2007117258 | A2 | | 10/2007 |
| WO | 2007130519 | A2 | | 11/2007 |
| WO | 2008145196 | A1 | | 12/2008 |

OTHER PUBLICATIONS

EPO Partial European Search Report, European Patent Application No. 11 176 258.9, Nov. 29, 2011.

EPO Communication Pursuant to Rule 69 EPC, European Patent Application No. 11 176 258.9, Apr. 23, 2012.

EPO Search Report and Search Opinion, European Patent Application No. 11 176 258.9, Mar. 16, 2012.

AU Examiner's First Report, Australian Patent Application No. 2005262317, Feb. 11, 2009.

AU Examiner's Second Report, Australian Patent Application No. 2005262317, May 29, 2009.

CIPO Office Action, Canadian Patent Application No. 2,573,532, Oct. 28, 2011.

JPO Office Action, Japanese Patent Application No. 2007-521628, Oct. 6, 2010.

JPO Notice of Allowance, Japanese Patent Application No. 2007-521628, Apr. 27, 2011.

PCT International Preliminary Report on Patentability, International Application No. PCT/US2005/024952, Jan. 25, 2007.

Ali et al., "Partial Sequence at 2BC region of HAV isolated from stool of acute sporadic HAV patients," The Journal of the Egyptian Health Association, 2002, 77(1-2):101-116.

Casas et al., "Detection of enteroviruses, hepatitis A virus and rotaviruses in sewage by means of an Immunomagnetic capture reverse transcription-PCR assay," Microbiol. Res., 2002, 157(3):169-176, Fischer, Jena, Germany.

Jean et al., "Detection of Hepatitis A Virus by the Nucleic Acid Sequence-Based Amplification Technique and Comparison with Reverse Transcription-PCR," Applied and Environmental Microbiology, 2001, 67(12):5593-5600, American Society for Microbiology, Washington D.C., USA.

Examiner's Report received in EP Patent Application 05 800 781.6 dated Aug. 3, 2009. (6 pages).

Beneduce et al., "Complete Nucleotide Sequence of a Cytopathic Hepatitis A Virus Strain Isolated in Italy," Virus Research, 1995, pp. 299-309, vol. 36, Elsevier Science B.V., London, UK.

Browne et al., "Binding studies of cationic thymidyl deoxyribonucleic guanidine to RNA homopolynucleotides," Biochemistry, Jul. 1995, pp. 7051-7055, vol. 92, Proc. Natl. Acad. Sci., USA.

Costa-Mattioli et al., "Quantification and duration of viraemia during hepatitis A infection as determined by real-time RT-PCR," J. Viral Hepatitis, 2002, pp. 101-106, vol. 9, Blackwell Science Ltd., San Francisco, CA.

Costa-Mattioli et al., "Genetic Variability of Hepatitis A Virus," J. Gen. Virology, 2003, pp. 3191-3201, vol. 84, part 12, Blackwell Science Ltd., San Francisco, CA.

Cristina et al., Genetic Variability and Molecular Evolution of Hepatitis A Virus, Virus Research 127, 2007, pp. 151-157, Science Direct, Elsevier Science Ltd., London, UK.

Cromeans et al., "Detection of Hepatitis A Virus RNA in Oyster Meat," Appl. Envir. Microbiol., Jun. 1997, pp. 2460-2463, vol. 63(6), American Society for Microbiology, Washington, D.C.

Dato et al., "Hepatitis A Outbreak Associated with Green Onions at a Restaurant—Monaca, Pennsylvania, 2003," Morbidity Mortality Wkly. Rpt., 2003, pp. 1155-1157, vol. 52(47), posted on the MMWR website (http://www.cdc.gov/mmwr), Centers for Disease Control and Prevention, Atlanta, GA.

Dempcy et al., "Synthesis of a thymidyl pentamer of deoxyribonucleic guanidine and binding studies with DNA homopolynucleotides," Proc. Natl. Acad. Sci. USA, 1995, pp. 6097-6101, vol. 92, National Academy of Sciences, Washington, D.C.

Fujiwara et al., "PCR-SSCP Analysis of 5'-Nontranslated Region of Hepatitis A Viral RNA: Comparison with Clinicopathological Features of Hepatitis A," Digestive Diseases and Sciences, Dec. 2000, pp. 2422-2427, vol. 45(12), Plenum Publishing Corporation, New York, NY.

Fujiwara et al., "Analysis of Full-Length Hepatitis A Virus Genome in Sera From Patients With Fulminant and Self-Limited Acute Type A Hepatitis," J. Hepatology, 2001, pp. 112-119, vol. 35, Elsevier Science B.V., London, UK.

Genbank Accession No. AB020564, Version No. AB020564.1, "Hepatitis A virus genomic RNA, complete sequence, isolate AH1," Aug. 14, 2001.

Genbank Accession No. AB020569, Version No. AB020569.1, "Hepatitis A virus genomic RNA, complete sequence, isolate FH3," Aug. 14, 2001.

Goswami-Biswendu et al., "Competitor Template RNA for Detection and Quantitation of Hepatitis A virus by PCR," Biotechniques, Jan. 1994, pp. 114-115, 118, 120-121, vol. 16(1), Informs Life Sciences Publishing, Westborough, MA, USA.

Gryaznov et al., "Oligodeoxyribonucleotide N3'-P5' Phosephoramidates: Synthesis and Hybridization Properties," J. Am. Chem. Soc., 1994, pp. 3143-3144, vol. 116, American Chemical Society, Washington, D.C.

Hu et al., "Complete Genomes of Two Human hepatitis A Virus Isolates from China: Analysis and Comparison with other Isolates," Acta Virol., 2002, pp. 153-157, vol. 46, AE Press, Ltd., Bratislava, Slovak Republic.

Hyrup et al., "Peptide Nucleic Acids (PNA): Synthesis, Properties and Potential Applications," Bioorganic & Medicinal Chemistry, 1996, pp. 5-23, vol. 4(1), Elsevier Science Ltd., London, UK.

Jansen et al., "Molecular Epidemiology of Human Hepatitis A Virus Defined by an Antigen-Capture Polymerase Chain Reaction Method," Proc. Natl. Acad. Sci., Apr. 1990, pp. 2867-2871, vol. 87, Medical Sciences, Little Rock, AR.

Koshkin et al., "LNA (Locked Nucleic Acid): An RNA Mimic Forming Exceedingly Stable LNA:LNA Duplexes," J. Am. Chem. Soc., 1998, pp. 13252-13253, vol. 120, American Chemical Society, Washington, D.C.

Laporte et al., "Foodborne Transmission of Hepatitis A—Massachusetts, 2001," Morbidity Mortality Wkly. Rpt., 2003, pp. 565-567, vol. 52(24), posted on the MMWR website (http://www.cdc.gov/mmwr), Centers for Disease Control and Prevention, Atlanta, GA, USA.

Li et al., "Detection of Enteroviruses and Hepatitis A Virus in Water by Consensus Primer Multiplex RT-PCR," World J. Gastroenterology, 2002, pp. 699-702, vol. 8(4), The WJG Press, Beijing, China.

Lin et al., "Synthesis and Duplex Stability of Oligonucleotides Containing Cytosine-Thymine Analogues," Nucleic Acids Research, 1989, pp. 10373-10383, vol. 17(24), Oxford University Press, Oxford, UK.

Lin et al., "Synthesis of Oligodeoxyribonucleotide Containing Degenerate Bases and Their Use As Primers in the Polymerase Chain Reaction," Nucleic Acid Research, 1992, pp. 5149-5152, vol. 20(19), Oxford University Press, Oxford, UK.

Majlessi et al., "Advantages of 2'-O-Methyl Oligoribonucleotide Probes for Detecting RNA Targets," Nucleic Acids Research, 1998, pp. 2224-2229, vol. 26(9), Oxford University Press, Oxford, UK.

Steffens et al., "Tricycle-DNA: A Phosphodiester-Backbone Based DNA Analog Exhibiting Strong Complementary Base-Pairing Properties," J. Am. Chem. Soc., 1997, pp. 11548-11549, vol. 119, American Chemical Society, Washington, D.C.

(56) References Cited

OTHER PUBLICATIONS

Stringfellow et al., Abstract P-553, “Simultaneous detection of parvovirus B19 and Hepatitis A Virus (HAV) in human plasma using a transcription-medicated amplification (TMA) assay,” The International Journal of Transfusion Medicine—Vox Sanguinis, Eds. Dana V. Cevine and Francine Decary, Aug. 2002, pp. 184, vol. 83(supp. 2), 27th Congress of the International Society of Blood Transfusion, Aug. 24-29, 2002, Vancouver, British Columbia.

Supplementary European Search Report, EP 05 80 0781, dated Feb. 2, 2009, 18 pages.

WHO/CDS/CSR/EDC/2000.7, “Hepatitis A,” World Health Organization—Department of Communicable Disease Surveillance and Response, 2000, pp. 1-41, document downloaded from the WHO/CSR website (http://www.who.int/emc), World Health Organization, Switzerland.

Najarian et al., “Primary structure and gene organization of human hepatitis A virus,” Biochemistry, May 1985, pp. 2627-2631, vol. 82, Proc.Natl.Acad.Sci., USA.

PCT Written Opinion and International Search Report, dated Jul. 17, 2006, 7 pages.

* cited by examiner

SEQUENCE LISTING

```
<160> NUMBER OF SEQ ID NOS: 174

<210> SEQ ID NO 1
<211> LENGTH: 54
<212> TYPE: DNA
<213> ORGANISM: Artificial Sequence
<220> FEATURE:
<223> OTHER INFORMATION: synthetic oligomer, capture probe

<400> SEQUENCE: 1

ggacuuccaa gaggggcucc gtttaaaaaa aaaaaaaaaa aaaaaaaaaa aaaa          54


<210> SEQ ID NO 2
<211> LENGTH: 60
<212> TYPE: DNA
<213> ORGANISM: Artificial Sequence
<220> FEATURE:
<223> OTHER INFORMATION: synthetic oligomer, capture probe

<400> SEQUENCE: 2

uuuagacucc uacagcucca ugcuaauttt aaaaaaaaaa aaaaaaaaaa aaaaaaaaaa     60


<210> SEQ ID NO 3
<211> LENGTH: 61
<212> TYPE: DNA
<213> ORGANISM: Artificial Sequence
<220> FEATURE:
<223> OTHER INFORMATION: synthetic oligomer, capture probe

<400> SEQUENCE: 3

uucauuucug uccauuucuc aucauucatt taaaaaaaaa aaaaaaaaaa aaaaaaaaaa     60

a                                                                     61
```

<210> SEQ ID NO 4
<211> LENGTH: 58
<212> TYPE: DNA
<213> ORGANISM: Artificial Sequence
<220> FEATURE:
<223> OTHER INFORMATION: synthetic oligomer, capture probe

<400> SEQUENCE: 4
gaaauugaau aguaaguucc accuctttaa aaaaaaaaaa aaaaaaaaaa aaaaaaaa 58

<210> SEQ ID NO 5
<211> LENGTH: 60
<212> TYPE: DNA
<213> ORGANISM: Artificial Sequence
<220> FEATURE:
<223> OTHER INFORMATION: synthetic oligomer, capture probe

<400> SEQUENCE: 5
gcauagcugc aggaaaauua aucauggttt aaaaaaaaaa aaaaaaaaaa aaaaaaaaaa 60

<210> SEQ ID NO 6
<211> LENGTH: 56
<212> TYPE: DNA
<213> ORGANISM: Artificial Sequence
<220> FEATURE:
<223> OTHER INFORMATION: synthetic oligomer, capture probe

<400> SEQUENCE: 6
gcauagcugc aggaaaauua aucttttaaaa aaaaaaaaaa aaaaaaaaaa aaaaaa 56

<210> SEQ ID NO 7
<211> LENGTH: 58
<212> TYPE: DNA
<213> ORGANISM: Artificial Sequence
<220> FEATURE:
<223> OTHER INFORMATION: synthetic oligomer, capture probe

<400> SEQUENCE: 7
gacaaaagaa aacuggagac uuucctttaa aaaaaaaaaa aaaaaaaaaa aaaaaaaa 58

<210> SEQ ID NO 8
<211> LENGTH: 21
<212> TYPE: DNA
<213> ORGANISM: Artificial Sequence
<220> FEATURE:
<223> OTHER INFORMATION: synthetic oligomer

<400> SEQUENCE: 8
ggacttccaa gaggggctcc g 21

<210> SEQ ID NO 9
<211> LENGTH: 27
<212> TYPE: DNA
<213> ORGANISM: Artificial Sequence
<220> FEATURE:
<223> OTHER INFORMATION: synthetic oligomer

<400> SEQUENCE: 9
tttagactcc tacagctcca tgctaat 27

<210> SEQ ID NO 10
<211> LENGTH: 28
<212> TYPE: DNA
<213> ORGANISM: Artificial Sequence
<220> FEATURE:
<223> OTHER INFORMATION: synthetic oligomer

```
<400> SEQUENCE: 10

ttcatttctg tccatttctc atcattca                                      28


<210> SEQ ID NO 11
<211> LENGTH: 25
<212> TYPE: DNA
<213> ORGANISM: Artificial Sequence
<220> FEATURE:
<223> OTHER INFORMATION: synthetic oligomer

<400> SEQUENCE: 11

gaaattgaat agtaagttcc acctc                                         25


<210> SEQ ID NO 12
<211> LENGTH: 27
<212> TYPE: DNA
<213> ORGANISM: Artificial Sequence
<220> FEATURE:
<223> OTHER INFORMATION: synthetic oliogmer

<400> SEQUENCE: 12

gcatagctgc aggaaaatta atcatgg                                       27


<210> SEQ ID NO 13
<211> LENGTH: 23
<212> TYPE: DNA
<213> ORGANISM: Artificial Sequence
<220> FEATURE:
<223> OTHER INFORMATION: synthetic oligomer

<400> SEQUENCE: 13

gcatagctgc aggaaaatta atc                                           23


<210> SEQ ID NO 14
<211> LENGTH: 25
<212> TYPE: DNA
<213> ORGANISM: Artificial Sequence
<220> FEATURE:
<223> OTHER INFORMATION: synthetic oligomer

<400> SEQUENCE: 14

gacaaaagaa aactggagac tttcc                                         25


<210> SEQ ID NO 15
<211> LENGTH: 23
<212> TYPE: DNA
<213> ORGANISM: Artificial Sequence
<220> FEATURE:
<223> OTHER INFORMATION: synthetic oligomer

<400> SEQUENCE: 15

ccatggtgag gggacttgat acc                                           23


<210> SEQ ID NO 16
<211> LENGTH: 22
<212> TYPE: DNA
<213> ORGANISM: Artificial Sequence
<220> FEATURE:
<223> OTHER INFORMATION: synthetic oligomer

<400> SEQUENCE: 16

cttgatacct caccgccgtt tg                                            22


<210> SEQ ID NO 17
<211> LENGTH: 23
<212> TYPE: DNA
```

<213> ORGANISM: Artificial Sequence
<220> FEATURE:
<223> OTHER INFORMATION: synthetic oligomer

<400> SEQUENCE: 17
ttgatacctc accgccgttt gcc 23

<210> SEQ ID NO 18
<211> LENGTH: 25
<212> TYPE: DNA
<213> ORGANISM: Artificial Sequence
<220> FEATURE:
<223> OTHER INFORMATION: synthetic oligomer

<400> SEQUENCE: 18
gatacctcac cgccgtttgc ctagg 25

<210> SEQ ID NO 19
<211> LENGTH: 27
<212> TYPE: DNA
<213> ORGANISM: Artificial Sequence
<220> FEATURE:
<223> OTHER INFORMATION: bacteriophage T7 promoter

<400> SEQUENCE: 19
aatttaatac gactcactat agggaga 27

<210> SEQ ID NO 20
<211> LENGTH: 49
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 20
aatttaatac gactcactat agggagaaga gaaacagatt aaagaaccc 49

<210> SEQ ID NO 21
<211> LENGTH: 53
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 21
aatttaatac gactcactat agggagagga agaaagaaga cagaaagcgt gaa 53

<210> SEQ ID NO 22
<211> LENGTH: 51
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 22
aatttaatac gactcactat agggagagga agaaagaaga cagaaagcgt g 51

```
<210> SEQ ID NO 23
<211> LENGTH: 50
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 23

aatttaatac gactcactat agggagagaa gaaagaagac agaaagcgtg                50


<210> SEQ ID NO 24
<211> LENGTH: 52
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 24

aatttaatac gactcactat agggagatgg aagaaagaag acagaaagcg tg             52


<210> SEQ ID NO 25
<211> LENGTH: 51
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 25

aatttaatac gactcactat agggagatgg aagaaagaag acagaaagcg t              51


<210> SEQ ID NO 26
<211> LENGTH: 51
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 26

aatttaatac gactcactat agggagactg gaagaaagaa gacagaaagc g              51


<210> SEQ ID NO 27
<211> LENGTH: 52
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 27

aatttaatac gactcactat agggagagca aggggagagc cctggaagaa ag             52
```

<210> SEQ ID NO 28
<211> LENGTH: 54
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 28
aatttaatac gactcactat agggagacag tatttataat ttcaacagtc acag 54

<210> SEQ ID NO 29
<211> LENGTH: 48
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 29
aatttaatac gactcactat agggagatct caacaaacca attatgtg 48

<210> SEQ ID NO 30
<211> LENGTH: 54
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promotet
<222> LOCATION: (1)..(27)
<223> OTHER INFORMATION:

<400> SEQUENCE: 30
aatttaatac gactcactat agggagacat gactctcaac aaaccaatta tgtg 54

<210> SEQ ID NO 31
<211> LENGTH: 51
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 31
aatttaatac gactcactat agggagacaa ttgcttcctt aacataaact g 51

<210> SEQ ID NO 32
<211> LENGTH: 53
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 32
aatttaatac gactcactat agggagacga tcaattgctt ccttaacata aac 53

```
<210> SEQ ID NO 33
<211> LENGTH: 47
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 33

aatttaatac gactcactat agggagacct tttcctctcc atgcctg                  47


<210> SEQ ID NO 34
<211> LENGTH: 52
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 34

aatttaatac gactcactat agggagagaa ttgaatttcc tccagcaaca tg            52


<210> SEQ ID NO 35
<211> LENGTH: 56
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 35

aatttaatac gactcactat agggagaaca agaattgaat ttcctccagc aacatg        56


<210> SEQ ID NO 36
<211> LENGTH: 54
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 36

aatttaatac gactcactat agggagaaca agaattgaat ttcctccagc aaca          54


<210> SEQ ID NO 37
<211> LENGTH: 52
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 37

aatttaatac gactcactat agggagacaa gaattgaatt tcctccagca ac            52
```

<210> SEQ ID NO 38
<211> LENGTH: 51
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 38
aatttaatac gactcactat agggagaaag aattgaattt cctccagcaa c 51

<210> SEQ ID NO 39
<211> LENGTH: 53
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 39
aatttaatac gactcactat agggagaaca agaattgaat ttcctccagc aac 53

<210> SEQ ID NO 40
<211> LENGTH: 52
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 40
aatttaatac gactcactat agggagacca caagaattga atttcctcca gc 52

<210> SEQ ID NO 41
<211> LENGTH: 52
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 41
aatttaatac gactcactat agggagactc tgagccaatc ttggatgaac tc 52

<210> SEQ ID NO 42
<211> LENGTH: 52
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 42
aatttaatac gactcactat agggagacag aacaattttc catcatgaca gt 52

<210> SEQ ID NO 43
<211> LENGTH: 55
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 43
aatttaatac gactcactat agggagaggt cataaaatct cattctccac caatc 55

<210> SEQ ID NO 44
<211> LENGTH: 56
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 44
aatttaatac gactcactat agggagagaa acactggtca taaaatctca ttctcc 56

<210> SEQ ID NO 45
<211> LENGTH: 52
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 45
aatttaatac gactcactat agggagaggt cacaaatgaa acactggtca ta 52

<210> SEQ ID NO 46
<211> LENGTH: 53
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 46
aatttaatac gactcactat agggagagaa aggtcacaaa tgaaacactg gtc 53

<210> SEQ ID NO 47
<211> LENGTH: 52
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 47
aatttaatac gactcactat agggagaaaa ggtcacaaat gaaacactgg tc 52

<210> SEQ ID NO 48
<211> LENGTH: 51
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 48
aatttaatac gactcactat agggagagaa aggtcacaaa tgaaacactg g 51

<210> SEQ ID NO 49
<211> LENGTH: 53
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 49
aatttaatac gactcactat agggagacaa atcatgaaag gtcacaaatg aaa 53

<210> SEQ ID NO 50
<211> LENGTH: 22
<212> TYPE: DNA
<213> ORGANISM: Artificial Sequence
<220> FEATURE:
<223> OTHER INFORMATION: synthetic oligomer, primer

<400> SEQUENCE: 50
agagaaacag attaaagaac cc 22

<210> SEQ ID NO 51
<211> LENGTH: 26
<212> TYPE: DNA
<213> ORGANISM: Artificial Sequence
<220> FEATURE:
<223> OTHER INFORMATION: synthetic oligomer, primer

<400> SEQUENCE: 51
ggaagaaaga agacagaaag cgtgaa 26

<210> SEQ ID NO 52
<211> LENGTH: 24
<212> TYPE: DNA
<213> ORGANISM: Artificial Sequence
<220> FEATURE:
<223> OTHER INFORMATION: synthetic oligomer, primer

<400> SEQUENCE: 52
ggaagaaaga agacagaaag cgtg 24

<210> SEQ ID NO 53
<211> LENGTH: 23
<212> TYPE: DNA
<213> ORGANISM: Artificial Sequence
<220> FEATURE:
<223> OTHER INFORMATION: synthetic oligomer, primer

<400> SEQUENCE: 53
gaagaaagaa gacagaaagc gtg 23

<210> SEQ ID NO 54
<211> LENGTH: 25
<212> TYPE: DNA
<213> ORGANISM: Artificial Sequence
<220> FEATURE:
<223> OTHER INFORMATION: synthetic oligomer, primer

<400> SEQUENCE: 54
tggaagaaag aagacagaaa gcgtg 25

<210> SEQ ID NO 55
<211> LENGTH: 24
<212> TYPE: DNA
<213> ORGANISM: Artificial Sequence
<220> FEATURE:
<223> OTHER INFORMATION: synthetic oligomer, primer

<400> SEQUENCE: 55
tggaagaaag aagacagaaa gcgt 24

<210> SEQ ID NO 56
<211> LENGTH: 24
<212> TYPE: DNA
<213> ORGANISM: Artificial Sequence
<220> FEATURE:
<223> OTHER INFORMATION: synthetic oligomer, primer

<400> SEQUENCE: 56
ctggaagaaa gaagacagaa agcg 24

<210> SEQ ID NO 57
<211> LENGTH: 25
<212> TYPE: DNA
<213> ORGANISM: Artificial Sequence
<220> FEATURE:
<223> OTHER INFORMATION: synthetic oligomer, primer

<400> SEQUENCE: 57
gcaaggggag agccctggaa gaaag 25

<210> SEQ ID NO 58
<211> LENGTH: 27
<212> TYPE: DNA
<213> ORGANISM: Artificial Sequence
<220> FEATURE:
<223> OTHER INFORMATION: synthetic oligomer, primer

<400> SEQUENCE: 58
cagtatttat aatttcaaca gtcacag 27

<210> SEQ ID NO 59
<211> LENGTH: 21
<212> TYPE: DNA
<213> ORGANISM: Artificial Sequence
<220> FEATURE:
<223> OTHER INFORMATION: synthetic oligomer, primer

<400> SEQUENCE: 59
tctcaacaaa ccaattatgt g 21

<210> SEQ ID NO 60
<211> LENGTH: 27
<212> TYPE: DNA
<213> ORGANISM: Artificial Sequence
<220> FEATURE:
<223> OTHER INFORMATION: synthetic oligomer, primer

<400> SEQUENCE: 60
catgactctc aacaaaccaa ttatgtg 27

<210> SEQ ID NO 61
<211> LENGTH: 24
<212> TYPE: DNA
<213> ORGANISM: Artificial Sequence
<220> FEATURE:
<223> OTHER INFORMATION: synthetic oligomer, primer

<400> SEQUENCE: 61
caattgcttc cttaacataa actg 24

<210> SEQ ID NO 62
<211> LENGTH: 26
<212> TYPE: DNA
<213> ORGANISM: Artificial Sequence
<220> FEATURE:
<223> OTHER INFORMATION: synthetic oligomer, primer

<400> SEQUENCE: 62
cgatcaattg cttccttaac ataaac 26

<210> SEQ ID NO 63
<211> LENGTH: 20
<212> TYPE: DNA
<213> ORGANISM: Artificial Sequence
<220> FEATURE:
<223> OTHER INFORMATION: synthetic oligomer, primer

<400> SEQUENCE: 63
ccttttcctc tccatgcctg 20

<210> SEQ ID NO 64
<211> LENGTH: 25
<212> TYPE: DNA
<213> ORGANISM: Artificial Sequence
<220> FEATURE:
<223> OTHER INFORMATION: synthetic oligomer, primer

<400> SEQUENCE: 64
gaattgaatt tcctccagca acatg 25

<210> SEQ ID NO 65
<211> LENGTH: 29
<212> TYPE: DNA
<213> ORGANISM: Artificial Sequence
<220> FEATURE:
<223> OTHER INFORMATION: synthetic oligomer, primer

<400> SEQUENCE: 65
acaagaattg aatttcctcc agcaacatg 29

<210> SEQ ID NO 66
<211> LENGTH: 27
<212> TYPE: DNA
<213> ORGANISM: Artificial Sequence
<220> FEATURE:
<223> OTHER INFORMATION: synthetic oligomer, primer

<400> SEQUENCE: 66
acaagaattg aatttcctcc agcaaca 27

<210> SEQ ID NO 67
<211> LENGTH: 25
<212> TYPE: DNA

<213> ORGANISM: Artificial Sequence
<220> FEATURE:
<223> OTHER INFORMATION: synthetic oligomer, primer

<400> SEQUENCE: 67
caagaattga atttcctcca gcaac 25

<210> SEQ ID NO 68
<211> LENGTH: 24
<212> TYPE: DNA
<213> ORGANISM: Artificial Sequence
<220> FEATURE:
<223> OTHER INFORMATION: synthetic oligomer, primer

<400> SEQUENCE: 68
aagaattgaa tttcctccag caac 24

<210> SEQ ID NO 69
<211> LENGTH: 26
<212> TYPE: DNA
<213> ORGANISM: Artificial Sequence
<220> FEATURE:
<223> OTHER INFORMATION: synthetic oligomer, primer

<400> SEQUENCE: 69
acaagaattg aatttcctcc agcaac 26

<210> SEQ ID NO 70
<211> LENGTH: 25
<212> TYPE: DNA
<213> ORGANISM: Artificial Sequence
<220> FEATURE:
<223> OTHER INFORMATION: synthetic oligomer, primer

<400> SEQUENCE: 70
ccacaagaat tgaatttcct ccagc 25

<210> SEQ ID NO 71
<211> LENGTH: 25
<212> TYPE: DNA
<213> ORGANISM: Artificial Sequence
<220> FEATURE:
<223> OTHER INFORMATION: synthetic oligomer, primer

<400> SEQUENCE: 71
ctctgagcca atcttggatg aactc 25

<210> SEQ ID NO 72
<211> LENGTH: 25
<212> TYPE: DNA
<213> ORGANISM: Artificial Sequence
<220> FEATURE:
<223> OTHER INFORMATION: synthetic oligomer, primer

<400> SEQUENCE: 72
cagaacaatt ttccatcatg acagt 25

<210> SEQ ID NO 73
<211> LENGTH: 28
<212> TYPE: DNA
<213> ORGANISM: Artificial Sequence
<220> FEATURE:
<223> OTHER INFORMATION: synthetic oligomer, primer

<400> SEQUENCE: 73
ggtcataaaa tctcattctc caccaatc 28

<210> SEQ ID NO 74
<211> LENGTH: 29
<212> TYPE: DNA
<213> ORGANISM: Artificial Sequence
<220> FEATURE:
<223> OTHER INFORMATION: synthetic oligomer, primer

<400> SEQUENCE: 74
gaaacactgg tcataaaatc tcattctcc 29

<210> SEQ ID NO 75
<211> LENGTH: 25
<212> TYPE: DNA
<213> ORGANISM: Artificial Sequence
<220> FEATURE:
<223> OTHER INFORMATION: synthetic oligomer, primer

<400> SEQUENCE: 75
ggtcacaaat gaaacactgg tcata 25

<210> SEQ ID NO 76
<211> LENGTH: 26
<212> TYPE: DNA
<213> ORGANISM: Artificial Sequence
<220> FEATURE:
<223> OTHER INFORMATION: synthetic oligomer, primer

<400> SEQUENCE: 76
gaaaggtcac aaatgaaaca ctggtc 26

<210> SEQ ID NO 77
<211> LENGTH: 25
<212> TYPE: DNA
<213> ORGANISM: Artificial Sequence
<220> FEATURE:
<223> OTHER INFORMATION: synthetic oligomer, primer

<400> SEQUENCE: 77
aaaggtcaca aatgaaacac tggtc 25

<210> SEQ ID NO 78
<211> LENGTH: 24
<212> TYPE: DNA
<213> ORGANISM: Artificial Sequence
<220> FEATURE:
<223> OTHER INFORMATION: synthetic oligomer, primer

<400> SEQUENCE: 78
gaaaggtcac aaatgaaaca ctgg 24

<210> SEQ ID NO 79
<211> LENGTH: 26
<212> TYPE: DNA
<213> ORGANISM: Artificial Sequence
<220> FEATURE:
<223> OTHER INFORMATION: synthetic oligomer, primer

<400> SEQUENCE: 79
caaatcatga aaggtcacaa atgaaa 26

<210> SEQ ID NO 80
<211> LENGTH: 19
<212> TYPE: DNA
<213> ORGANISM: Artificial Sequence
<220> FEATURE:
<223> OTHER INFORMATION: synthetic oligomer, primer

<400> SEQUENCE: 80
gacttgatac ctcaccgcc 19

<210> SEQ ID NO 81
<211> LENGTH: 23
<212> TYPE: DNA
<213> ORGANISM: Artificial Sequence
<220> FEATURE:
<223> OTHER INFORMATION: synthetic oligomer, primer

<400> SEQUENCE: 81
acttgatacc tcaccgccgt ttg 23

<210> SEQ ID NO 82
<211> LENGTH: 23
<212> TYPE: DNA
<213> ORGANISM: Artificial Sequence
<220> FEATURE:
<223> OTHER INFORMATION: synthetic oligomer, primer

<400> SEQUENCE: 82
cttgatacct caccgccgtt tgc 23

<210> SEQ ID NO 83
<211> LENGTH: 24
<212> TYPE: DNA
<213> ORGANISM: Artificial Sequence
<220> FEATURE:
<223> OTHER INFORMATION: synthetic oligomer, primer

<400> SEQUENCE: 83
cttgatacct caccgccgtt tgcc 24

<210> SEQ ID NO 84
<211> LENGTH: 22
<212> TYPE: DNA
<213> ORGANISM: Artificial Sequence
<220> FEATURE:
<223> OTHER INFORMATION: synthetic oligomer, primer

<400> SEQUENCE: 84
cuugatacct caccgccgtt tg 22

<210> SEQ ID NO 85
<211> LENGTH: 23
<212> TYPE: DNA
<213> ORGANISM: Artificial Sequence
<220> FEATURE:
<223> OTHER INFORMATION: synthetic oligomer, primer

<400> SEQUENCE: 85
cuugatacct caccgccgtt tgc 23

<210> SEQ ID NO 86
<211> LENGTH: 26
<212> TYPE: DNA
<213> ORGANISM: Artificial Sequence
<220> FEATURE:
<223> OTHER INFORMATION: synthetic oligomer, primer

<400> SEQUENCE: 86
gcagatagaa tgcttggatt gtctgg 26

<210> SEQ ID NO 87
<211> LENGTH: 25
<212> TYPE: DNA

<213> ORGANISM: Artificial Sequence
<220> FEATURE:
<223> OTHER INFORMATION: synthetic oligomer, primer

<400> SEQUENCE: 87
gcagatagaa tgcttggatt gtctg 25

<210> SEQ ID NO 88
<211> LENGTH: 25
<212> TYPE: DNA
<213> ORGANISM: Artificial Sequence
<220> FEATURE:
<223> OTHER INFORMATION: synthetic oligomer, primer

<400> SEQUENCE: 88
cagatagaat gcttggattg tctgg 25

<210> SEQ ID NO 89
<211> LENGTH: 30
<212> TYPE: DNA
<213> ORGANISM: Artificial Sequence
<220> FEATURE:
<223> OTHER INFORMATION: synthetic oligomer, primer

<400> SEQUENCE: 89
tctcctttta taatagcaac ttcaaattgg 30

<210> SEQ ID NO 90
<211> LENGTH: 29
<212> TYPE: DNA
<213> ORGANISM: Artificial Sequence
<220> FEATURE:
<223> OTHER INFORMATION: synthetic oligomer, primer

<400> SEQUENCE: 90
ctccttttat aatagcaact tcaaattgg 29

<210> SEQ ID NO 91
<211> LENGTH: 25
<212> TYPE: DNA
<213> ORGANISM: Artificial Sequence
<220> FEATURE:
<223> OTHER INFORMATION: synthetic oligomer, primer

<400> SEQUENCE: 91
ttataatagc aacttcaaat tggtc 25

<210> SEQ ID NO 92
<211> LENGTH: 20
<212> TYPE: DNA
<213> ORGANISM: Artificial Sequence
<220> FEATURE:
<223> OTHER INFORMATION: synthetic oligomer, primer

<400> SEQUENCE: 92
ggcaacatta gtgacaactg 20

<210> SEQ ID NO 93
<211> LENGTH: 27
<212> TYPE: DNA
<213> ORGANISM: Artificial Sequence
<220> FEATURE:
<223> OTHER INFORMATION: synthetic oligomer, primer

<400> SEQUENCE: 93
ggcaacatta gtgacaactg ttaatgg 27

<210> SEQ ID NO 94
<211> LENGTH: 18
<212> TYPE: DNA
<213> ORGANISM: Artificial Sequence
<220> FEATURE:
<223> OTHER INFORMATION: synthetic oligomer, primer

<400> SEQUENCE: 94
caggcatgga gaggaaaa 18

<210> SEQ ID NO 95
<211> LENGTH: 20
<212> TYPE: DNA
<213> ORGANISM: Artificial Sequence
<220> FEATURE:
<223> OTHER INFORMATION: synthetic oligomer, primer

<400> SEQUENCE: 95
caggcatgga gaggaaaagg 20

<210> SEQ ID NO 96
<211> LENGTH: 19
<212> TYPE: DNA
<213> ORGANISM: Artificial Sequence
<220> FEATURE:
<223> OTHER INFORMATION: synthetic oligomer, primer

<400> SEQUENCE: 96
caggcatgga gaggaaaag 19

<210> SEQ ID NO 97
<211> LENGTH: 18
<212> TYPE: DNA
<213> ORGANISM: Artificial Sequence
<220> FEATURE:
<223> OTHER INFORMATION: synthetic oligomer, primer

<400> SEQUENCE: 97
ggcatggaga ggaaaagg 18

<210> SEQ ID NO 98
<211> LENGTH: 23
<212> TYPE: DNA
<213> ORGANISM: Artificial Sequence
<220> FEATURE:
<223> OTHER INFORMATION: synthetic oligomer, primer

<400> SEQUENCE: 98
taagaaaatt gaaatgcaga gaa 23

<210> SEQ ID NO 99
<211> LENGTH: 26
<212> TYPE: DNA
<213> ORGANISM: Artificial Sequence
<220> FEATURE:
<223> OTHER INFORMATION: synthetic oligomer, primer

<400> SEQUENCE: 99
ctccaaaacg ctttttagaa agagtc 26

<210> SEQ ID NO 100
<211> LENGTH: 22
<212> TYPE: DNA
<213> ORGANISM: Artificial Sequence
<220> FEATURE:
<223> OTHER INFORMATION: synthetic oligomer

<400> SEQUENCE: 100
ccatgattaa ttttcctgca gc 22

<210> SEQ ID NO 101
<211> LENGTH: 26
<212> TYPE: DNA
<213> ORGANISM: Artificial Sequence
<220> FEATURE:
<223> OTHER INFORMATION: synthetic oligomer, primer

<400> SEQUENCE: 101
ccaaaacgct ttttagaaag agtccc 26

<210> SEQ ID NO 102
<211> LENGTH: 25
<212> TYPE: DNA
<213> ORGANISM: Artificial Sequence
<220> FEATURE:
<223> OTHER INFORMATION: synthetic oligomer, primer

<400> SEQUENCE: 102
cgctgagttt gagcagaatt tagaa 25

<210> SEQ ID NO 103
<211> LENGTH: 28
<212> TYPE: DNA
<213> ORGANISM: Artificial Sequence
<220> FEATURE:
<223> OTHER INFORMATION: synthetic oligomer, primer

<400> SEQUENCE: 103
ctgagtttga gcagaattta gaaaatgc 28

<210> SEQ ID NO 104
<211> LENGTH: 24
<212> TYPE: DNA
<213> ORGANISM: Artificial Sequence
<220> FEATURE:
<223> OTHER INFORMATION: synthetic oligomer, primer

<400> SEQUENCE: 104
atgcatggct atgagtttta tcag 24

<210> SEQ ID NO 105
<211> LENGTH: 26
<212> TYPE: DNA
<213> ORGANISM: Artificial Sequence
<220> FEATURE:
<223> OTHER INFORMATION: synthetic oligomer, primer

<400> SEQUENCE: 105
gcatggctat gagttttatc agaaat 26

<210> SEQ ID NO 106
<211> LENGTH: 27
<212> TYPE: DNA
<213> ORGANISM: Artificial Sequence
<220> FEATURE:
<223> OTHER INFORMATION: synthetic oligomer, primer

<400> SEQUENCE: 106
gcauggctat gagttttatc agaaatt 27

<210> SEQ ID NO 107
<211> LENGTH: 26
<212> TYPE: DNA

<213> ORGANISM: Artificial Sequence
<220> FEATURE:
<223> OTHER INFORMATION: synthetic oligomer, primer

<400> SEQUENCE: 107
catggctatg agttttatca gaaatt 26

<210> SEQ ID NO 108
<211> LENGTH: 27
<212> TYPE: DNA
<213> ORGANISM: Artificial Sequence
<220> FEATURE:
<223> OTHER INFORMATION: synthetic oligomer, primer

<400> SEQUENCE: 108
gcatggctat gagttttatc agaaatt 27

<210> SEQ ID NO 109
<211> LENGTH: 20
<212> TYPE: DNA
<213> ORGANISM: Artificial Sequence
<220> FEATURE:
<223> OTHER INFORMATION: synthetic oligomer probe

<400> SEQUENCE: 109
gccgtttgcc taggctatag 20

<210> SEQ ID NO 110
<211> LENGTH: 20
<212> TYPE: DNA
<213> ORGANISM: Artificial Sequence
<220> FEATURE:
<223> OTHER INFORMATION: synthetic oligomer

<400> SEQUENCE: 110
ctatagccta ggcaaacggc 20

<210> SEQ ID NO 111
<211> LENGTH: 25
<212> TYPE: DNA
<213> ORGANISM: Artificial Sequence
<220> FEATURE:
<223> OTHER INFORMATION: synthetic oligomer probe

<400> SEQUENCE: 111
cagggttctt taatctgttt ctcta 25

<210> SEQ ID NO 112
<211> LENGTH: 25
<212> TYPE: DNA
<213> ORGANISM: Artificial Sequence
<220> FEATURE:
<223> OTHER INFORMATION: synthetic oligomer

<400> SEQUENCE: 112
tagagaaaca gattaaagaa ccctg 25

<210> SEQ ID NO 113
<211> LENGTH: 27
<212> TYPE: DNA
<213> ORGANISM: Artificial Sequence
<220> FEATURE:
<223> OTHER INFORMATION: synthetic oligomer, probe

<400> SEQUENCE: 113
atgatgtttg gatttcatca ttctgtg 27

<210> SEQ ID NO 114
<211> LENGTH: 27
<212> TYPE: DNA
<213> ORGANISM: Artificial Sequence
<220> FEATURE:
<223> OTHER INFORMATION: synthetic oligomer

<400> SEQUENCE: 114
cacagaatga tgaaatccaa acatcat 27

<210> SEQ ID NO 115
<211> LENGTH: 22
<212> TYPE: DNA
<213> ORGANISM: Artificial Sequence
<220> FEATURE:
<223> OTHER INFORMATION: synthetic oligomer, probe

<400> SEQUENCE: 115
ggtcaaatcc aagtccaaaa ac 22

<210> SEQ ID NO 116
<211> LENGTH: 22
<212> TYPE: DNA
<213> ORGANISM: Artificial Sequence
<220> FEATURE:
<223> OTHER INFORMATION: synthetic oligomer

<400> SEQUENCE: 116
gtttttggac ttggatttga cc 22

<210> SEQ ID NO 117
<211> LENGTH: 20
<212> TYPE: RNA
<213> ORGANISM: Artificial Sequence
<220> FEATURE:
<223> OTHER INFORMATION: synthetic oligomer, probe

<400> SEQUENCE: 117
ccuauguuaa uuucugaggg 20

<210> SEQ ID NO 118
<211> LENGTH: 20
<212> TYPE: DNA
<213> ORGANISM: Artificial Sequence
<220> FEATURE:
<223> OTHER INFORMATION: synthetic oligomer

<400> SEQUENCE: 118
ccctcagaaa ttaacatagg 20

<210> SEQ ID NO 119
<211> LENGTH: 20
<212> TYPE: RNA
<213> ORGANISM: Artificial Sequence
<220> FEATURE:
<223> OTHER INFORMATION: synthetic oligomer, probe

<400> SEQUENCE: 119
caggcaugga gaggaaaagg 20

<210> SEQ ID NO 120
<211> LENGTH: 20
<212> TYPE: DNA
<213> ORGANISM: Artificial Sequence
<220> FEATURE:
<223> OTHER INFORMATION: synthetic oligomer

<400> SEQUENCE: 120 cctttcctc tccatgcctg 20

<210> SEQ ID NO 121
<211> LENGTH: 23
<212> TYPE: RNA
<213> ORGANISM: Artificial Sequence
<220> FEATURE:
<223> OTHER INFORMATION: synthetic oligomer, probe

<400> SEQUENCE: 121
ggucuuccug gaaugugugg ugg 23

<210> SEQ ID NO 122
<211> LENGTH: 23
<212> TYPE: RNA
<213> ORGANISM: Artificial Sequence
<220> FEATURE:
<223> OTHER INFORMATION: synthetic oligomer, probe

<400> SEQUENCE: 122
gucuuccugg aaugugugu ggg 23

<210> SEQ ID NO 123
<211> LENGTH: 21
<212> TYPE: DNA
<213> ORGANISM: Artificial Sequence
<220> FEATURE:
<223> OTHER INFORMATION: synthetic oligomer, probe

<400> SEQUENCE: 123
tcttcctgga atgtgtggtg g 21

<210> SEQ ID NO 124
<211> LENGTH: 21
<212> TYPE: DNA
<213> ORGANISM: Artificial Sequence
<220> FEATURE:
<223> OTHER INFORMATION: synthetic oligomer, probe

<400> SEQUENCE: 124
tcuuccugga augugugug g 21

<210> SEQ ID NO 125
<211> LENGTH: 20
<212> TYPE: DNA
<213> ORGANISM: Artificial Sequence
<220> FEATURE:
<223> OTHER INFORMATION: synthetic oligomer

<400> SEQUENCE: 125
caccacacat tccaggaaga 20

<210> SEQ ID NO 126
<211> LENGTH: 20
<212> TYPE: DNA
<213> ORGANISM: Artificial Sequence
<220> FEATURE:
<223> OTHER INFORMATION: synthetic oligomer, probe

<400> SEQUENCE: 126
cttcctggaa tgtgtggtgg 20

<210> SEQ ID NO 127
<211> LENGTH: 20
<212> TYPE: RNA

<213> ORGANISM: Artificial Sequence
<220> FEATURE:
<223> OTHER INFORMATION: synthetic oligomer, probe

<400> SEQUENCE: 127
cuuccuggaa ugugugugg 20

<210> SEQ ID NO 128
<211> LENGTH: 22
<212> TYPE: RNA
<213> ORGANISM: Artificial Sequence
<220> FEATURE:
<223> OTHER INFORMATION: synthetic oligomer, probe

<400> SEQUENCE: 128
gcugcaggaa aauuaaucau gg 22

<210> SEQ ID NO 129
<211> LENGTH: 26
<212> TYPE: DNA
<213> ORGANISM: Artificial Sequence
<220> FEATURE:
<223> OTHER INFORMATION: synthetic oligomer, probe

<400> SEQUENCE: 129
tggagaaaga gaugauagaa uauagg 26

<210> SEQ ID NO 130
<211> LENGTH: 24
<212> TYPE: RNA
<213> ORGANISM: Artificial Sequence
<220> FEATURE:
<223> OTHER INFORMATION: synthetic oligomer, probe

<400> SEQUENCE: 130
ggagaaugag auuuuaugac cagu 24

<210> SEQ ID NO 131
<211> LENGTH: 24
<212> TYPE: DNA
<213> ORGANISM: Artificial Sequence
<220> FEATURE:
<223> OTHER INFORMATION: synthetic oligomer

<400> SEQUENCE: 131
actggtcata aaatctcatt ctcc 24

<210> SEQ ID NO 132
<211> LENGTH: 28
<212> TYPE: DNA
<213> ORGANISM: Artificial Sequence
<220> FEATURE:
<223> OTHER INFORMATION: synthetic oligomer, primer
<220> FEATURE:
<221> NAME/KEY: Cla I site
<222> LOCATION: (3)..(8)
<223> OTHER INFORMATION:
<220> FEATURE:
<221> NAME/KEY: Cla I recognition site
<222> LOCATION: (3)..(8)
<223> OTHER INFORMATION:

<400> SEQUENCE: 132
ccatcgatgc gttttggaga ctacattc 28

<210> SEQ ID NO 133
<211> LENGTH: 29
<212> TYPE: DNA

<213> ORGANISM: Artificial Sequence
<220> FEATURE:
<223> OTHER INFORMATION: synthetic oligomer, primer
<220> FEATURE:
<221> NAME/KEY: Pst I recognition site
<222> LOCATION: (4)..(9)
<223> OTHER INFORMATION:

<400> SEQUENCE: 133
aaactgcaga tgaaggttcc tacaattcc 29

<210> SEQ ID NO 134
<211> LENGTH: 29
<212> TYPE: DNA
<213> ORGANISM: Artificial Sequence
<220> FEATURE:
<223> OTHER INFORMATION: synthetic oligomer, primer
<220> FEATURE:
<221> NAME/KEY: Kpn I recognition site
<222> LOCATION: (4)..(9)
<223> OTHER INFORMATION:

<400> SEQUENCE: 134
cggggtaccg cgttttggag actacattc 29

<210> SEQ ID NO 135
<211> LENGTH: 29
<212> TYPE: DNA
<213> ORGANISM: Artificial Sequence
<220> FEATURE:
<223> OTHER INFORMATION: synthetic oligomer, primer
<220> FEATURE:
<221> NAME/KEY: Pst I recognition site
<222> LOCATION: (4)..(9)
<223> OTHER INFORMATION:

<400> SEQUENCE: 135
aaactgcaga gaggtggaac ttactattc 29

<210> SEQ ID NO 136
<211> LENGTH: 38
<212> TYPE: RNA
<213> ORGANISM: Artificial Sequence
<220> FEATURE:
<223> OTHER INFORMATION: synthetic oligomer

<400> SEQUENCE: 136
uuaagccuau auucuaucau cucuuucucc aaacagga 38

<210> SEQ ID NO 137
<211> LENGTH: 27
<212> TYPE: DNA
<213> ORGANISM: Artificial Sequence
<220> FEATURE:
<223> OTHER INFORMATION: synthetic oligomer

<400> SEQUENCE: 137
gccccaccac acauuccagg aagacct 27

<210> SEQ ID NO 138
<211> LENGTH: 42
<212> TYPE: DNA
<213> ORGANISM: Artificial Sequence
<220> FEATURE:
<223> OTHER INFORMATION: synthetic oligomer

<400> SEQUENCE: 138
gcaaggggag agccctggaa gaaagaagac agaaagcgtg aa 42

<210> SEQ ID NO 139
<211> LENGTH: 8
<212> TYPE: DNA
<213> ORGANISM: Artificial Sequence
<220> FEATURE:
<223> OTHER INFORMATION: synthetic oligomer

<400> SEQUENCE: 139 gaagaaag 8

<210> SEQ ID NO 140
<211> LENGTH: 21
<212> TYPE: DNA
<213> ORGANISM: Artificial Sequence
<220> FEATURE:
<223> OTHER INFORMATION: synthetic oligomer

<400> SEQUENCE: 140
gaagaaagaa gacagaaagc g 21

<210> SEQ ID NO 141
<211> LENGTH: 42
<212> TYPE: DNA
<213> ORGANISM: Artificial Sequence
<220> FEATURE:
<223> OTHER INFORMATION: synthetic oligomer

<400> SEQUENCE: 141
ccatggtgag gggacttgat acctcaccgc cgtttgccta gg 42

<210> SEQ ID NO 142
<211> LENGTH: 9
<212> TYPE: DNA
<213> ORGANISM: Artificial Sequence
<220> FEATURE:
<223> OTHER INFORMATION: synthetic oligomer

<400> SEQUENCE: 142 cttgatacc 9

<210> SEQ ID NO 143
<211> LENGTH: 11
<212> TYPE: DNA
<213> ORGANISM: Artificial Sequence
<220> FEATURE:
<223> OTHER INFORMATION: synthetic oligomer

<400> SEQUENCE: 143
gacttgatac c 11

<210> SEQ ID NO 144
<211> LENGTH: 22
<212> TYPE: DNA
<213> ORGANISM: Artificial Sequence
<220> FEATURE:
<223> OTHER INFORMATION: synthetic oligomer

<400> SEQUENCE: 144
cttgatacct caccgccgtt tg 22

<210> SEQ ID NO 145
<211> LENGTH: 19
<212> TYPE: DNA
<213> ORGANISM: Artificial Sequence
<220> FEATURE:
<223> OTHER INFORMATION: synthetic oligomer

<400> SEQUENCE: 145
gatacctcac cgccgtttg 19

<210> SEQ ID NO 146
<211> LENGTH: 17
<212> TYPE: DNA
<213> ORGANISM: Artificial Sequence
<220> FEATURE:
<223> OTHER INFORMATION: synthetic oligomer

<400> SEQUENCE: 146
cttgatacct caccgcc 17

<210> SEQ ID NO 147
<211> LENGTH: 28
<212> TYPE: DNA
<213> ORGANISM: Artificial Sequence
<220> FEATURE:
<223> OTHER INFORMATION: synthetic oligomer

<400> SEQUENCE: 147
cgatcaattg cttccttaac ataaactg 28

<210> SEQ ID NO 148
<211> LENGTH: 22
<212> TYPE: DNA
<213> ORGANISM: Artificial Sequence
<220> FEATURE:
<223> OTHER INFORMATION: synthetic oligomer

<400> SEQUENCE: 148
caattgcttc cttaacataa ac 22

<210> SEQ ID NO 149
<211> LENGTH: 31
<212> TYPE: DNA
<213> ORGANISM: Artificial Sequence
<220> FEATURE:
<223> OTHER INFORMATION: synthetic oligomer

<400> SEQUENCE: 149
ccacaagaat tgaatttcct ccagcaacat g 31

<210> SEQ ID NO 150
<211> LENGTH: 19
<212> TYPE: DNA
<213> ORGANISM: Artificial Sequence
<220> FEATURE:
<223> OTHER INFORMATION: synthetic oligomer

<400> SEQUENCE: 150
gaattgaatt tcctccagc 19

<210> SEQ ID NO 151
<211> LENGTH: 58
<212> TYPE: DNA
<213> ORGANISM: Artificial Sequence
<220> FEATURE:
<223> OTHER INFORMATION: synthetic oligomer

<400> SEQUENCE: 151
caaatcatga aaggtcacaa atgaaacact ggtcataaaa tctcattctc caccaatc 58

<210> SEQ ID NO 152
<211> LENGTH: 20
<212> TYPE: DNA

```
<213> ORGANISM: Artificial Sequence
<220> FEATURE:
<223> OTHER INFORMATION: synthetic oligomer

<400> SEQUENCE: 152

ggtcacaaat gaaacactgg                                                20


<210> SEQ ID NO 153
<211> LENGTH: 23
<212> TYPE: DNA
<213> ORGANISM: Artificial Sequence
<220> FEATURE:
<223> OTHER INFORMATION: synthetic oligomer

<400> SEQUENCE: 153

aaaggtcaca aatgaaacac tgg                                            23


<210> SEQ ID NO 154
<211> LENGTH: 12
<212> TYPE: DNA
<213> ORGANISM: Artificial Sequence
<220> FEATURE:
<223> OTHER INFORMATION: synthetic oligomer

<400> SEQUENCE: 154

gaaacactgg tc                                                        12


<210> SEQ ID NO 155
<211> LENGTH: 21
<212> TYPE: DNA
<213> ORGANISM: Artificial Sequence
<220> FEATURE:
<223> OTHER INFORMATION: synthetic oligomer

<400> SEQUENCE: 155

ggtcataaaa tctcattctc c                                              21


<210> SEQ ID NO 156
<211> LENGTH: 24
<212> TYPE: DNA
<213> ORGANISM: Artificial Sequence
<220> FEATURE:
<223> OTHER INFORMATION: synthetic oligomer

<400> SEQUENCE: 156

cagatagaat gcttggattg tctg                                           24


<210> SEQ ID NO 157
<211> LENGTH: 32
<212> TYPE: DNA
<213> ORGANISM: Artificial Sequence
<220> FEATURE:
<223> OTHER INFORMATION: synthetic oligomer

<400> SEQUENCE: 157

tctcctttta taatagcaac ttcaaattgg tc                                  32


<210> SEQ ID NO 158
<211> LENGTH: 23
<212> TYPE: DNA
<213> ORGANISM: Artificial Sequence
<220> FEATURE:
<223> OTHER INFORMATION: synthetic oligomer

<400> SEQUENCE: 158

ttataatagc aacttcaaat tgg                                            23
```

<210> SEQ ID NO 159
<211> LENGTH: 16
<212> TYPE: DNA
<213> ORGANISM: Artificial Sequence
<220> FEATURE:
<223> OTHER INFORMATION: synthetic oligomer

<400> SEQUENCE: 159
ggcatggaga ggaaaa 16

<210> SEQ ID NO 160
<211> LENGTH: 17
<212> TYPE: DNA
<213> ORGANISM: Artificial Sequence
<220> FEATURE:
<223> OTHER INFORMATION: synthetic oligomer

<400> SEQUENCE: 160
ggcatggaga ggaaaag 17

<210> SEQ ID NO 161
<211> LENGTH: 28
<212> TYPE: DNA
<213> ORGANISM: Artificial Sequence
<220> FEATURE:
<223> OTHER INFORMATION: synthetic oligomer

<400> SEQUENCE: 161
ctccaaaacg ctttttagaa agagtccc 28

<210> SEQ ID NO 162
<211> LENGTH: 24
<212> TYPE: DNA
<213> ORGANISM: Artificial Sequence
<220> FEATURE:
<223> OTHER INFORMATION: synthetic oligomer

<400> SEQUENCE: 162
ccaaaacgct ttttagaaag agtc 24

<210> SEQ ID NO 163
<211> LENGTH: 30
<212> TYPE: DNA
<213> ORGANISM: Artificial Sequence
<220> FEATURE:
<223> OTHER INFORMATION: synthetic oligomer

<400> SEQUENCE: 163
cgctgagttt gagcagaatt tagaaaatgc 30

<210> SEQ ID NO 164
<211> LENGTH: 23
<212> TYPE: DNA
<213> ORGANISM: Artificial Sequence
<220> FEATURE:
<223> OTHER INFORMATION: synthetic oligomer

<400> SEQUENCE: 164
ctgagtttga gcagaattta gaa 23

<210> SEQ ID NO 165
<211> LENGTH: 29
<212> TYPE: DNA
<213> ORGANISM: Artificial Sequence
<220> FEATURE:
<223> OTHER INFORMATION: synthetic oligomer

<400> SEQUENCE: 165
atgcatggct atgagtttta tcagaaatt 29

<210> SEQ ID NO 166
<211> LENGTH: 21
<212> TYPE: DNA
<213> ORGANISM: Artificial Sequence
<220> FEATURE:
<223> OTHER INFORMATION: synthetic oligomer

<400> SEQUENCE: 166
catggctatg agttttatca g 21

<210> SEQ ID NO 167
<211> LENGTH: 22
<212> TYPE: DNA
<213> ORGANISM: Artificial Sequence
<220> FEATURE:
<223> OTHER INFORMATION: synthetic oligomer

<400> SEQUENCE: 167
gcatggctat gagttttatc ag 22

<210> SEQ ID NO 168
<211> LENGTH: 25
<212> TYPE: DNA
<213> ORGANISM: Artificial Sequence
<220> FEATURE:
<223> OTHER INFORMATION: synthetic oligomer

<400> SEQUENCE: 168
catggctatg agttttatca gaaat 25

<210> SEQ ID NO 169
<211> LENGTH: 58
<212> TYPE: DNA
<213> ORGANISM: Artificial Sequence
<220> FEATURE:
<223> OTHER INFORMATION: synthetic oligomer, capture probe

<400> SEQUENCE: 169
gttggctata cctaaagtca tgaatcctaa aaaaaaaaaa aaaaaaaaaa aaaaaaa 58

<210> SEQ ID NO 170
<211> LENGTH: 21
<212> TYPE: DNA
<213> ORGANISM: Artificial Sequence
<220> FEATURE:
<223> OTHER INFORMATION: synthetic oligomer, primer

<400> SEQUENCE: 170
cccctagaaa acccatcctc t 21

<210> SEQ ID NO 171
<211> LENGTH: 52
<212> TYPE: DNA
<213> ORGANISM: Artificial Sequence
<220> FEATURE:
<223> OTHER INFORMATION: synthetic oligomer, promoter primer
<220> FEATURE:
<221> NAME/KEY: promoter
<222> LOCATION: (1)..(27)
<223> OTHER INFORMATION:

<400> SEQUENCE: 171
aatttaatac gactcactat agggagaagt accgggtagt tgtacgctaa ct 52

```
<210> SEQ ID NO 172
<211> LENGTH: 25
<212> TYPE: DNA
<213> ORGANISM: Artificial Sequence
<220> FEATURE:
<223> OTHER INFORMATION: synthetic oligomer, primer

<400> SEQUENCE: 172

agtaccgggt agttgtacgc taact                                    25


<210> SEQ ID NO 173
<211> LENGTH: 20
<212> TYPE: RNA
<213> ORGANISM: Artificial Sequence
<220> FEATURE:
<223> OTHER INFORMATION: synthetic oligomer, probe

<400> SEQUENCE: 173

gucauggaca guuaucugac                                          20


<210> SEQ ID NO 174
<211> LENGTH: 22
<212> TYPE: RNA
<213> ORGANISM: Artificial Sequence
<220> FEATURE:
<223> OTHER INFORMATION: synthetic oligomer, probe

<400> SEQUENCE: 174

guauuaucua gugaagacuu ac                                       22
```

COMPOSITIONS AND METHODS FOR DETECTION OF HEPATITIS A VIRUS NUCLEIC ACID

RELATED APPLICATIONS

This application is a continuation of U.S. patent application Ser. No. 12/429,589, filed Apr. 24, 2009, now allowed, which is a division of U.S. Pat. No. 7,544,792, filed Jul. 13, 2005, and claims the benefit under 35 U.S.C. §119(e) of U.S. Provisional patent application No. 60/587,734, filed Jul. 13, 2004, all of which are incorporated herein by reference in their entirety.

FIELD OF THE INVENTION

This invention relates to diagnostic detection of a human virus, and specifically relates to assays to detect human hepatitis A virus sequences by using in vitro nucleic acid amplification and detection of amplified sequences.

BACKGROUND OF THE INVENTION

Hepatitis A virus (HAV) is the causative agent of one form of hepatitis that may produce symptoms that include fever, fatigue, nausea, abdominal pain, diarrhea, loss of appetite, and jaundice over less than two months. Of those infected with HAV, about 10% to 15% have a prolonged or relapsing symptoms over a six to nine months following infection Immunity to HAV, based on the individual's production of anti-HAV immunoglobulin G (IgG), follows both symptomatic and asymptomatic infections.

Although the incidence of HAV infections has dramatically decreased in parts of the world in which vaccination for HAV (e.g., by using inactivated HAV) has been widely used since the late 1990's, epidemics of HAV infections (greater than 700 cases per 100,000 population) may occur in non-immune populations where poor sanitary conditions exist, even temporarily, e.g. following an earthquake. HAV is shed in feces of infected persons and is usually transmitted by the fecal-oral route. Community-wide outbreaks may result from food-borne transmission that occurs when an HAV-infected food handler contaminates food during preparation, or when food materials are contaminated during growing, harvesting, packing, or processing in the distribution system. Transmission may also result from contact with HAV-contaminated serum, blood products, or contaminated needles, e.g., by transfusion or injection drug use. Persons at risk of HAV infection include those who have household or sex contacts with HAV-infected persons, persons who have clotting-factor disorders (e.g., hemophilia) or chronic liver disease, persons who travel in countries where hepatitis A is common, men who have sex with men, illegal drug users, and children who live in areas with high rates of hepatitis A (e.g., >20 cases per 100,000 population).

HAV is a 27-nm RNA virus (*picornavirus*) that contains a plus-sense single-stranded RNA genome of about 7.5 kb, for which a single serotype has been found worldwide. HAV replicates in the liver, is excreted in bile, and is shed in feces during the acute phase of an infection (up to 10.sup.8 virus per ml). The incubation period is usually two to six weeks before symptoms appear. Diagnosis of hepatitis A cannot be differentiated from other types of viral hepatitis by symptoms or other clinical features (e.g., elevated serum aminotransferase levels). Typically, hepatitis A diagnosis is confirmed by serological testing that provides positive results for the presence of anti-HAV immunoglobulins (Ig). Anti-HAV IgM is generally present five to ten days before the onset of symptoms and is undetectable in most patients by six months later, whereas anti-HAV IgG appears early during infection and remains detectable for the individual's lifetime. HAV RNA can be detected in the blood and stool of most persons during the acute phase of infection by using nucleic acid testing methods, e.g., amplification by the polymerase chain reaction (PCR), and nucleic acid sequencing, which has been used to identify the genetic relatedness of HAV following community-wide infections (Dato et al., Morbidity Mortality Wkly. Rpt., 2003, 52(47): 1155-57; LaPorte et al., Morbidity Mortality Wkly. Rpt., 2003, 52(24): 565-67). These methods, however, are not generally used for diagnostic purposes.

In the USA, about 100 persons die each year from acute liver failure due to hepatitis A (death rate of about 0.015%). Even in nonfatal hepatitis A cases there are substantial costs associated with HAV infections, including the costs of patient hospitalization, outpatient visits, and lost workdays. Public health costs associated with hepatitis A outbreaks include locating and administering immune globulin to people exposed to an infected individual or infectious source (e.g., contaminated water or food) within two weeks of exposure. Substantial psychological costs and economic losses may result from the perceived risk of infection, particularly for community-wide outbreaks. Because of the relative ease of HAV transmission in contaminated food and water, and the morbidity associated with hepatitis A, HAV is a potential agent for use in biological terrorism.

There exists a need to accurately detect the presence of HAV in biological and environmental samples. There exists a need to rapidly diagnose HAV-infected individuals. For example, because immune globulin must be administered to a person within two weeks of HAV exposure to be effective, there exists a need for a rapid and accurate assay to promptly evaluate food handlers with hepatitis symptoms and report HAV-positive sources to public health agencies. There is a need to detect HAV present in contaminated materials, such as water and food, to prevent community-wide outbreaks or epidemics resulting from use or consumption of these materials. There is also a need to detect HAV contamination in products that may be used in medical treatment, e.g., blood or serum used for transfusions or for the manufacture of factors derived from human fluids.

The present invention responds to these needs by disclosing oligonucleotide sequences used in nucleic acid testing methods to detect the presence of HAV nucleic acid (HAV RNA or cDNA derived from RNA) in a sample.

SUMMARY OF THE INVENTION

The invention includes nucleic acid oligomers useful for purification, amplification and detection of HAV target sequences. Such oligomers or combinations of oligomers may be contained in a kit configuration, embodiments of which may include additional oligomers and/or other reagents for amplifying and/or detecting a HAV sequence. The invention also includes methods of detecting HAV in a sample that use steps of purifying HAV nucleic acid from other components in the sample, amplifying a HAV RNA target sequence or cDNA made therefrom by using a nucleic acid polymerase in vitro and any combination of amplification oligomers as described herein to produce an amplified product, and detecting the amplified product by using a detection probe that hybridizes specifically with at least a portion of the amplified product. In one embodiment, HAV nucleic acid is purified by using at least one capture oligomer that includes a sequence that hybridizes specifically to a HAV RNA target region to form a hybridization complex that includes the HAV RNA being separated from other sample components.

One aspect of the invention is a combination of at least two oligomers specific for amplifying a HAV target region that include: for a first HAV target region, an oligomer of about 23 to 26 nt contained in the sequence of SEQ ID NO: 138 that includes at least the sequence of SEQ ID NO: 139 or SEQ ID NO: 140, or an oligomer in a size range of about 19 to 25 nt contained in the sequence of SEQ ID NO: 141 and that contains at least one sequence of SEQ ID NOS: 142 to 146, or a promoter primer oligomer in a size range of about 50 to 53 nt that includes a HAV target-specific portion of any one of SEQ ID NOS: 21 to 27; for a second HAV target region, an oligomer of about 21 to 27 nt contained in the sequence of SEQ ID NO: 60 or contained in the sequence of SEQ ID NO: 86 that includes at least the sequence of SEQ ID NO: 156, or a promoter primer oligomer in a size range of about 48 to 54 nt that includes a HAV target-specific portion of any one of SEQ ID NOS: 29 to 32; for a third HAV target region, an oligomer of about 24 to 30 nt contained in the sequence of SEQ ID NO: 147 that includes at least the sequence of SEQ ID NO: 148, or is contained in the sequence of SEQ ID NO: 157 and that includes at least the sequence of SEQ ID NO: 158, or a promoter primer oligomer that includes a HAV target-specific portion of SEQ ID NO: 31 or SEQ ID NO: 32; for a fourth HAV target region, an oligomer of about 18 to 27 nt contained in the sequence of SEQ ID NO: 93 or SEQ ID NO: 95 and that contains at least the sequence of SEQ ID NO: 97, SEQ ID NO: 159, or SEQ ID NO: 160, or a promoter primer oligomer that includes a HAV target-specific portion of SEQ ID NO: 33; for a fifth HAV target region, an oligomer of about 19 to 31 nt contained in the sequence of SEQ ID NO: 149 and that includes at least the sequence of SEQ ID NO: 150, or a promoter primer oligomers in a size range of about 51 to 56 nt that includes a HAV target-specific portion of any one of SEQ ID NOS: 34 to 40; for a sixth HAV target region, an oligomer of about 24 to 28 nt contained in the sequence of SEQ ID NO: 161 and that include at least the sequence of SEQ ID NO: 162, or a promoter primer oligomer that includes a HAV target-specific portion of SEQ ID NO: 41 or SEQ ID NO: 42; for a seventh HAV target region, an oligomer of about 20 to 30 nt contained in the sequence of SEQ ID NO: 151 and that includes at least any one of the sequences of SEQ ID NO: 152 to SEQ ID NO: 155, or is contained in SEQ ID NO: 163 and includes at least the sequence of SEQ ID NO: 164, or is contained in SEQ ID NO: 165 and includes at least any one of the sequences of SEQ ID NOS: 166 to 168, or a promoter primer oligomer in a size range of about 51 to 56 nt and that includes a HAV target-specific portion of any one of SEQ ID NOS: 43 to 49; and a second amplification oligomer. Preferred embodiments of combinations of at least two oligomers specific for the first HAV target region are selected from SEQ ID NO: 15, SEQ ID NO: 16, SEQ ID NO: 17, SEQ ID NO: 18, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 80, SEQ ID NO: 81, SEQ ID NO: 82, SEQ ID NO: 83, SEQ ID NO: 84, SEQ ID NO: 85, SEQ ID NO: 143, SEQ ID NO: 144, and SEQ ID NO: 145. Preferred embodiments of combinations of at least two oligomers specific for the second HAV target region are selected from SEQ ID NO: 28, SEQ ID NO: 29, SEQ ID NO: 30, SEQ ID NO: 31, SEQ ID NO: 32, SEQ ID NO: 58, SEQ ID NO: 59, SEQ ID NO: 60, SEQ ID NO: 86, SEQ ID NO: 87, SEQ ID NO: 88, and SEQ ID NO: 156. Preferred embodiments of combinations of at least two oligomers specific for the third HAV target region are selected from SEQ ID NO: 31, SEQ ID NO: 32, SEQ ID NO: 61, SEQ ID NO: 62, SEQ ID NO: 89, SEQ ID NO: 90, SEQ ID NO: 91, and SEQ ID NO: 148. Preferred embodiments of combinations of at least two oligomers specific for the fourth HAV target region are selected from SEQ ID NO: 33, SEQ ID NO: 63, SEQ ID NO: 92, SEQ ID NO: 93, SEQ ID NO: 94, SEQ ID NO: 95, SEQ ID NO: 96, and SEQ ID NO: 97. Preferred embodiments of combinations of at least two oligomers specific for the fifth HAV target region are selected from SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 97, SEQ ID NO: 149, and SEQ ID NO: 150. Preferred combinations of at least two oligomers specific for the sixth HAV target region are selected from SEQ ID NO: 41, SEQ ID NO: 42, SEQ ID NO: 71, SEQ ID NO: 72, SEQ ID NO: 98, SEQ ID NO: 99, SEQ ID NO: 101, SEQ ID NO: 161, and SEQ ID NO: 162. Preferred combinations of at least two oligomers specific for the seventh HAV target region are selected from SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 102, SEQ ID NO: 103, SEQ ID NO: 104, SEQ ID NO: 104, SEQ ID NO: 106, SEQ ID NO: 107, SEQ ID NO: 108, SEQ ID NO: 152, SEQ ID NO: 153, SEQ ID NO: 155, SEQ ID NO: 163, SEQ ID NO: 164, SEQ ID NO: 165, SEQ ID NO: 166, SEQ ID NO: 167, and SEQ ID NO: 168.

Other preferred embodiments further comprising at least one capture probe oligomer selected from the group consisting of SEQ ID NOS: 1 to 7 and SEQ ID NOS: 8-14 linked to a moiety that allows it to bind a solid support. In one aspect of this embodiment, the binding moiety is a substantially homopolymeric nucleic acid sequence. In one aspect of this embodiment, the solid support is a magnetic bead. Still other embodiments further include at least one detection probe oligomer selected from SEQ ID NO: 109, SEQ ID NO: 111, SEQ ID NO: 113, SEQ ID NO: 115, SEQ ID NO: 117, SEQ ID NO: 119, SEQ ID NO: 121 to SEQ ID NO: 124, and SEQ ID NO: 126 to SEQ ID NO: 130. Preferred embodiments of combinations of oligomers include at least two oligomers specific for amplifying a selected HAV target region and at least one detection probe oligomer that is specific for a sequence contained in HAV genomic sequence located between the selected two oligomers specific for amplifying the selected HAV target region. Preferred embodiments of such combinations of oligomers may be packaged together in a kit, which may further contain other reagents such as reagents used in purifying HAV RNA from a sample and/or reagents used in in vitro nucleic acid amplification, and/or reagents used in producing a detectable signal from a detection probe oligomer.

Another aspect of the invention is a method of detecting the presence of HAV in a sample that includes the steps of purifying HAV nucleic acid from other components in a sample containing HAV; amplifying a HAV target sequence in the purified HAV nucleic acid, or a cDNA made therefrom, by using an in vitro amplification reaction that includes at least two amplification oligomers specific for a selected HAV target region, which include: for a first HAV target region, an oligomer of about 23 to 26 nt contained in the sequence of SEQ ID NO: 138 and that includes at least the sequence of SEQ ID NO: 139 or SEQ ID NO: 140, or an oligomer in a size range of about 19 to 25 nt contained in the sequence of SEQ ID NO: 141 and that contains at least one sequence of SEQ ID NOS: 142 to 146, or a promoter primer oligomer in a size range of about 50 to 53 nt that includes a HAV target-specific portion of any one of SEQ ID NOS: 21 to 27; for a second HAV target region, an oligomer of about 21 to 27 nt contained in the sequence of SEQ ID NO: 60 or contained in the sequence of SEQ ID NO: 86 and that includes at least the sequence of SEQ ID NO: 156, or a promoter primer oligomer in a size range of about 48 to 54 nt that includes a HAV target-specific portion of any one of SEQ ID NOS: 29 to 32; for a third HAV target region, an oligomer of about 24 to 30 nt contained in the sequence of SEQ ID NO: 147 and that includes at least the sequence of SEQ ID NO: 148, or contained in the sequence of SEQ ID NO: 157 and that includes at least the sequence of SEQ ID NO: 158, or a promoter primer oligomer that includes a HAV target-specific portion of SEQ ID NO: 31 or SEQ ID NO: 32; for a fourth HAV target region, an oligomer of about 18 to 27 nt contained in the sequence of SEQ ID NO: 93 or SEQ ID NO: 95 and that contains at least the sequence of SEQ ID NO: 97, SEQ ID NO: 159, or SEQ ID NO: 160, or a promoter primer oligomer that includes a HAV target-specific portion of SEQ ID NO: 33; for a fifth HAV target region, an oligomer of about 19 to 31 nt contained in the sequence of SEQ ID NO: 149 and that includes at least the sequence of SEQ ID NO: 150, or a promoter primer oligomer in a size range of about 51 to 56 nt that includes a HAV target-specific portion of any one of SEQ ID NOS: 34 to 40; for a sixth HAV target region, an oligomer of about 24 to 28 nt contained in the sequence of SEQ ID NO: 161 and that includes at least the sequence of SEQ ID NO: 162, or a promoter primer oligomer that includes a HAV target-specific portion of SEQ ID NO: 41 or SEQ ID NO: 42; for a seventh HAV target region, an oligomer of about 20 to 30 nt contained in the sequence of SEQ ID NO: 151 and that includes at least any one of the sequences of SEQ ID NO: 152 to SEQ ID NO: 155, or is contained in SEQ ID NO: 163 and includes at least the sequence of SEQ ID NO: 164, or is contained in SEQ ID NO: 165 and includes at least any one of the sequences of SEQ ID NOS: 166 to 168, or a promoter primer oligomer in a size range of about 51 to 56 nt and that includes a HAV target-specific portion of any one of SEQ ID NOS: 43 to 49; and a second amplification oligomer, to produce an amplified product of the selected HAV target region; and detecting the amplified product. Preferably, the detecting step is performed by using a nucleic acid detection probe comprising a target hybridizing region that hybridizes specifically with at least a portion of the amplified product.

A preferred embodiment in the purifying step contacts the sample with at least one capture probe oligomer selected from the group consisting of SEQ ID NOS: 1 to 7 and SEQ ID NOS: 8-14 linked to a moiety that allows it to bind a solid support, wherein a target hybridization sequence of said at least one capture probe oligomer hybridizes specifically to a sequence in HAV RNA to form a hybridization complex with the HAV RNA, and can be used with a solid support to separate the HAV RNA from other sample components. Preferred embodiments that amplify a sequence in the first HAV target region use at least two oligomers specific for the first HAV target region selected from SEQ ID NO: 15, SEQ ID NO: 16, SEQ ID NO: 17, SEQ ID NO: 18, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 80, SEQ ID NO: 81, SEQ ID NO: 82, SEQ ID NO: 83, SEQ ID NO: 84, SEQ ID NO: 85, SEQ ID NO: 143, SEQ ID NO: 144, and SEQ ID NO: 145; and then use at least one detection probe that hybridizes specifically to the amplified product of the first HAV target region. Preferred embodiments that amplify a sequence in the second HAV target region use at least two oligomers specific for the second HAV target region selected from SEQ ID NO: 28, SEQ ID NO: 29, SEQ ID NO: 30, SEQ ID NO: 31, SEQ ID NO: 32, SEQ ID NO: 58, SEQ ID NO: 59, SEQ ID NO: 60, SEQ ID NO: 86, SEQ ID NO: 87, SEQ ID NO: 88, and SEQ ID NO: 156; and then use at least one detection probe that hybridizes specifically to the amplified product of the second HAV target region. Preferred embodiments that amplify a sequence in the third HAV target region use at least two oligomers specific for the third HAV target region selected from SEQ ID NO: 31, SEQ ID NO: 32, SEQ ID NO: 61, SEQ ID NO: 62, SEQ ID NO: 89, SEQ ID NO: 90, SEQ ID NO: 91, and SEQ ID NO: 148; and then use at least one detection probe that hybridizes specifically to the amplified product of the third HAV target region. Preferred embodiments that amplify a sequence in the fourth HAV target region use at least two oligomers specific for the fourth HAV target region selected from SEQ ID NO: 33, SEQ ID NO: 63, SEQ ID NO: 92, SEQ ID NO: 93, SEQ ID NO: 94, SEQ ID NO: 95, SEQ ID NO: 96, and SEQ ID NO: 97; and then use at least one detection probe that hybridizes specifically to the amplified product of the fourth HAV target region. Preferred embodiments that amplify a sequence in the fifth HAV target region use at least two oligomers specific for the fifth HAV target region selected from SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 97, SEQ ID NO: 149, and SEQ ID NO: 150; and then use at least one detection probe that hybridizes specifically to the amplified product of the fifth HAV target region. Preferred embodiments that amplify a sequence in the sixth HAV target region use at least two oligomers specific for the sixth HAV target region selected from SEQ ID NO: 41, SEQ ID NO: 42, SEQ ID NO: 71, SEQ ID NO: 72, SEQ ID NO: 98, SEQ ID NO: 99, SEQ ID NO: 101, SEQ ID NO: 161, and SEQ ID NO: 162; and then used at least one detection probe that hybridizes specifically to the amplified product of the sixth HAV target region. Preferred embodiments that amplify a sequence in the seventh HAV target region use at least two oligomers specific for the seventh HAV target region selected from SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 102, SEQ ID NO: 103, SEQ ID NO: 104, SEQ ID NO: 104, SEQ ID NO: 106, SEQ ID NO: 107, SEQ ID NO: 108, SEQ ID NO: 152, SEQ ID NO: 153, SEQ ID NO: 155, SEQ ID NO: 163, SEQ ID NO: 164, SEQ ID NO: 165, SEQ ID NO: 166, SEQ ID NO: 167, and SEQ ID NO: 168; and then use at least one detection probe that hybridizes specifically to the amplified product of the seventh HAV target region. In one aspect of this preferred method, the nucleic acid detection oligomer comprises a target hybridizing region nucleic acid sequence consisting essentially of a nucleic acid sequence selected from the group consisting of SEQ ID NO: 109, SEQ ID NO: 111, SEQ ID NO: 113, SEQ ID NO: 115, SEQ ID NO: 117, SEQ ID NO: 119, SEQ ID NO: 121 to SEQ ID NO: 124, and SEQ ID NO: 126 to SEQ ID NO: 130. In one aspect of this preferred method the nucleic acid detection oligomer further comprises a 2'-O-methyl linkages, a chemiluminescent label, an acridinium ester label, a synthetic linker or combinations thereof.

DETAILED DESCRIPTION OF THE INVENTION

The present invention includes methods of detecting HAV present in samples. These samples may be biological samples derived from humans (e.g., feces, blood, serum, saliva or urine), environmental samples (e.g., water, soil) or other materials (e.g., foodstuffs) that are potentially contaminated with HAV. A sample includes any liquid that may contain HAV or solid that may contain or have surface HAV. Samples include, for example, those from environmental sources such as water, biological sources such a human fluids or wastes, and food, packaging materials, or other components used in food processing. A biological sample includes any tissue or material derived from a living or dead human which may contain HAV or HAV nucleic acid, including, for example, saliva, blood, plasma, serum, biopsy tissue, gastrointestinal tissue, urine, feces, or other body fluids, tissues or materials. A sample may be treated to physically or mechanically disrupt its physical state to release HAV particles or HAV RNA into an aqueous solution or solvent by using standard methods.

The present invention encompasses nucleic acid compositions, such as oligomers that hybridize specifically to HAV RNA or nucleic acids derived from HAV RNA, e.g., cDNA or amplified sequences made from HAV RNA. One such composition is a capture oligomer used to purify HAV RNA from a complex mixture such as a sample by hybridizing specifically to HAV RNA and attaching the hybridized HAV RNA to a capture support that permits separation of the captured HAV RNA from other sample components. The method of purification that uses such a capture oligomer is generally referred to as target capture, where HAV RNA is the specific target nucleic acid. Another oligomer of the invention is a nucleic acid amplification oligomer (sometimes referred to as a primer). Additional embodiments include probe oligomers that hybridize specifically to HAV RNA or amplified HAV nucleic acid sequences to provide a signal that detects the presence of an HAV specific sequence. These nucleic acid sequences are useful for capturing, amplifying and detecting HAV specific sequences and, thus, function together for detecting the presence of HAV in a sample.

The methods are based on detecting the presence of HAV nucleic acid sequences by amplifying in vitro a region of the HAV genome and detecting the amplified nucleic acid by using a probe that binds specifically to a sequence in the amplified nucleic acid. One embodiment of the method includes a step of isolating or purifying HAV nucleic acid from a sample before the step of amplifying a region of the HAV genome. This embodiment isolates HAV genomic RNA by using a capture oligomer that binds specifically to a sequence in the HAV genome, preferably outside of the region of the HAV genome that is amplified, and separating the complex made up of the capture oligomer and the bound HAV RNA from other sample components by using a capture support, such as a particle to which the capture oligomer also binds. Amplifying a portion of the HAV genomic sequence uses one or more amplification oligomers that bind specifically to HAV RNA or a complementary sequence, and enzymatic synthesis in vitro to make additional copies of a portion of the HAV genomic sequence or a complementary sequence by using the amplification oligomers as primers for synthesis of the additional copies. A preferred embodiment uses an isothermal amplification reaction to make additional copies of a portion of the HAV genomic sequence. The amplified HAV sequence is then detected by specifically binding one or more probe oligomers to the amplified nucleic acid and detecting a signal that results from the probe oligomer bound to the amplified sequence. Detection of a signal resulting from the probe oligomer bound to the amplified HAV sequence indicates the presence of HAV in the sample. These method are useful for detecting the presence of HAV in a variety of samples, such as biological samples used to diagnose a HAV infection in a human, or HAV-contaminated environmental samples to prevent the spread of HAV resulting from use or consumption of the contaminated source. These methods are also useful for testing human fluid samples for the presence of HAV, such as in serum or plasma, to prevent subsequent HAV infections resulting from use of the human fluid in transfusion or for preparation of therapeutic factors. The methods of the present invention are also useful for screening human tissue or organs for the presence of HAV to prevent their use in transplantation therapy. Thus, these methods are especially important for detecting HAV contamination in human samples or products derived from human tissue.

Nucleic acids include DNA or an analog thereof, RNA or an analog thereof, or mixed DNA-RNA polymers or oligomers, made up of at least two, and preferably ten or more bases linked by a backbone structure. DNA and RNA may be made up of the common bases (A, T, G and C for DNA, and A, G, C and U for RNA), although base analogs (e.g., inosine) and abasic positions (i.e., a phosphodiester backbone that lacks a nucleotide at one or more positions, see U.S. Pat. No. 5,585,481) are also included in these terms. Polymers may be many hundreds or thousands of nucleotides long, whereas oligomers generally refer to nucleic acids of 1,000 or fewer linked nucleotides, and often comprise two to about 100 linked nucleotides. Oligomers generally fall in a size range having a lower limit of about 10 bases and an upper limit of about 150 bases, preferably in a size range of about 15 to about 70 bases. Oligomers may be purified from naturally occurring biological sources, but preferably are synthesized in vitro using any of a variety of well-known enzymatic or chemical methods (e.g., Caruthers et al., 1987, Methods in Enzymol., 154: 287).

A nucleic acid backbone refers to groups or linkages known in the art (Eschenmoser, 1999, Science 284:2118-2124), e.g., sugar-phosphodiester linkages, 2'-O-methyl linkages, guanidine linkers in DNA ("DNG"), S-methylthiourea linkers, methylphosphonate linkages, phosphoramidate linkages, amide backbone modifications as in polyamide or peptide nucleic acids (PNA), phosphorothioate linkages, phosphonic ester nucleic acid linkages, pyranosyl oligonucleotide linkages, bicyclo- and tricyclo-nucleic acid linkages, formacetal and 3'-thioformacetal linkages, morpholino linkages, or other modifications of the natural phosphodiester internucleoside bond, or combinations thereof (Majlessi et al., 1998, Nucl. Acids Res. 26(9):2224-2229; Dempcy et al., 1995, Proc. Natl. Acad. Sci. USA 92:6097-6101; Browne et al., 1995, Proc. Natl. Acad. Sci. USA 92:7051-7055; Arya & Bruice, 1998, J. Am. Chem. Soc. 120:6619-6620; Reynolds et al., 1996, Nucl. Acids Res. 24(22):4584-4591; Gryaznov & Chen, 1994, Am. Chem. Soc. 116:3143-3144; Chaturvedi et al., 1996, Nucl. Acids Res. 24(12):2318-2323; Hyrup & Nielsen, 1996, Bioorg. & Med. Chem. 4:5-23; Hydig-Hielsen et al., PCT Pat. App. WO 95/32305; Mesmaeker et al., Syn. Left., November 1997:1287-1290; Peyman et al., 1996, Angew. Chem. Int. Ed. Engl. 35(22):2636-2638; Aerschot et al., 1995, Angew. Chem. Int. Ed. Engl. 34(12):1338-1339; Koshkin et al., 1998, J. Am. Chem. Soc. 120:13252-13253; Steffens & Leumann, 1997, J. Am. Chem. Soc. 119:11548-11549; Jones et al., 1993, J. Org. Chem. 58:2983-2991; Summerton & Weller, 1997, Antisense & Nucl. Acid Drug Dev. 7:187-195; Stirchak et al., 1989, Nucl. Acids Res. 17(15):

6129-6141). A nucleic acid backbone may include a mixture of linkages in the same oligomer or polymer (e.g., one or more sugar-phosphodiester linkages and one or more 2'-O-methyl linkages in the strand) or may have the same linkages throughout the strand (e.g., all 2'-O-methyl or all amide modification linkages).

A target, target sequence, or target nucleic acid may refer to a large sequence (e.g., greater than 1000 nt) or a smaller sequence within a larger nucleic acid, to which another sequence binds, e.g., by using standard complementary base pairing. A target nucleic acid may be RNA or DNA, which is naturally occurring or made synthetically. For example, a target may be a relatively large nucleic acid such as the HAV genome, or a target may be a smaller subsequence contained in HAV RNA, its complement, or an amplification product made from it, which binds specifically another sequence in an oligomer. Those skilled in the art will appreciate that a target nucleic acid may exist in any form, e.g., a sense or antisense (+ or −) strand.

Complementary nucleic acids (or nucleic acid complementarity) refers to a base sequence in one strand of nucleic acid that, due to orientation of its functional groups, binds to a base sequence in an opposing strand, e.g., by hydrogen bonding between A and T or U bases, and between C and G bases. Substantially complementary means that a base sequence in one strand is not completely or perfectly complementary to a base sequence in an opposing strand, but that sufficient bonding occurs between bases of the two strands to form a stable hybridized complex in a set of conditions (e.g., salt concentration in an aqueous solution, or a temperature). Such conditions may be predicted by using the base sequences and standard mathematical calculations known to those skilled in the art for determining the melting temperature (Tm) at which 50% of hybridized strands are denatured, or by empirical determination of Tm by using routine methods (e.g., see Sambrook et al., Molecular Cloning, A Laboratory Manual, 2nd Ed., (Cold Spring Harbor Laboratory, Cold Spring Harbor, N.Y., 1989), at 9.50-51, 11.46-49, 11.55-57).

A hybridization condition refers to the cumulative environment in which one nucleic acid strand bonds to a second nucleic acid strand by complementary strand interactions to produce a hybridization complex. Such conditions include, e.g., temperature, chemical components and concentrations of compounds (e.g., salts, buffers, chelating agents, organic compounds) in aqueous and/or organic solutions that contain the nucleic acids. Other factors, such incubation time or reaction chamber dimensions may contribute to hybridization conditions, which are well known in the art (e.g., see Sambrook et al., Id., at 1.90-1.91, 9.47-9.51, 11.47-11.57).

A label refers to a molecular moiety that is detectable or produces a detectable response directly or indirectly, e.g., by catalyzing a reaction that produces a signal. Labels include luminescent moieties (e.g., fluorescent, bioluminescent, or chemiluminescent compounds), radioisotopes, members of binding pairs (e.g., biotin and avidin or streptavidin), enzymes or enzyme substrates, reactive groups or chromophores, e.g., a dye or particle that results in a detectable color. A detectable response or signal is any perceptible or measurable output that indicates the presence of a label, e.g., light, color, radioactive decay emission, electrical signal, magnetic field, or signal blockage, such as from quenching or turbidity.

An immobilized oligomer or probe refers to an oligomer that is connected or attached, covalently or noncovalently, to a capture support matrix, which provides a means for joining a capture hybrid containing a target nucleic acid to the capture support. A preferred immobilized probe is an oligomer that binds, directly or indirectly, to a target nucleic acid to facilitate separation of the bound target nucleic acid from unbound sample materials. In one embodiment, the target is indirectly bound to the immobilized probe via a capture probe that links the target and immobilized probe in a hybridization complex (see U.S. Pat. Nos. 6,110,678 and 6,280,952, Weisburg et al.). Any of a variety of supports may be used, such as matrices or particles made of, e.g., nitrocellulose, nylon, glass, polyacrylate, mixed polymers, polystyrene, silane polypropylene, and magnetic materials. Monodisperse magnetic particles of relatively uniform size that can be readily retrieved from solution by applying a magnetic force are a preferred embodiment of a support.

A capture oligomer or probe joins a target nucleic acid and an immobilized probe, i.e., by using a target-specific moiety that binds the target sequence and a moiety that attaches the capture probe to an immobilized probe. In one embodiment, both attachments result from hybridization of complementary base sequences, i.e., hybridization of a target sequence with a target-complementary sequence of the capture probe, and hybridization of another portion of the capture probe to a complementary sequence of the immobilized probe. In other embodiments, one or more attachments may occur by using members of a specific binding pair (e.g., biotin and avidin or streptavidin), which are well-known in the art. Compositions and methods that use capture probes are known (U.S. Pat. No. 6,110,678).

Separating or purifying refers to removing one or more components of a sample from other sample components. Sample components include nucleic acids in a generally aqueous solution phase, which may also include materials such as proteins, carbohydrates, lipids, and other compounds. Preferably, separating or purifying a nucleic acid removes at least about 70%, more preferably at least about 90% and, even more preferably, at least about 95% of the nucleic acid from other sample components.

An amplification oligonucleotide or oligomer refers to an oligomer that hybridizes to a target nucleic acid, or its complementary sequence, and participates in a nucleic acid amplification reaction by serving as a primer for synthesis of nucleic acid in vitro. Amplification oligomers may contain additional functional sequences, such a promoter sequence that binds an RNA polymerase in an oligomer referred to as a promoter primer. An amplification oligonucleotide generally contains at least about 10 contiguous bases, and preferably at least about 12 contiguous bases, that are complementary to a target sequence (or a complementary strand thereof). The contiguous bases are preferably at least about 80%, more preferably at least about 90%, and most preferably about 100% complementary to the sequence that binds to the amplification oligomer. An amplification oligomer may be RNA, DNA, or mixed DNA-RNA bases, and optionally may include modified nucleotides or backbone linkages.

A primer refers to an oligonucleotide that hybridizes to a template nucleic acid and which has an end (usually 3') that can be extended in a polymerization reaction catalyzed by an enzyme. The 5' region of the primer may be non-complementary to the target nucleic acid, e.g., as in a promoter primer that includes a 5' promoter sequence that is not present in the target sequence. Those skilled in the art will appreciate that a promoter primer may function as a primer independent of its promoter sequence (i.e., with or without the promoter sequence) and that any amplification oligomer may be modified to include a 5' promoter sequence, and thus function as a promoter primer.

Amplification refers to any known procedure for obtaining multiple copies of a target sequence, its complement, or fragments thereof. Amplification of fragments refers to production of an amplified nucleic acid that contains less than the complete target nucleic acid sequence or its complement, e.g., amplification of a portion of the complete HAV genome. Amplification of a fragment or portion of the complete target may result from using an amplification oligomer that which hybridizes to, and initiates polymerization from an internal position of the target nucleic acid. Known amplification methods include, e.g., transcription-mediated amplification (TMA), replicase-mediated amplification, the polymerase chain reaction (PCR), ligase chain reaction (LCR) and strand-displacement amplification (SDA). Replicase-mediated amplification uses self-replicating RNA molecules, and a replicase such as QB-replicase (e.g., U.S. Pat. No. 4,786,600 Kramer et al.). PCR uses a DNA polymerase, multiple primers and thermal cycling to synthesize many copies of two complementary strands of DNA or cDNA (e.g., U.S. Pat. Nos. 4,683,195, 4,683,202, and 4,800,159, Mullis et al.). LCR uses at least four separate oligomers to amplify a target and its complementary strand by using multiple cycles of hybridization, ligation, and denaturation (e.g., U.S. Pat. Nos. 5,427,930 Biekenmeyer et al., and 5,494,810 Barany et al.). SDA uses a primer that contains a recognition site for a restriction endonuclease and the endonuclease nicks one strand of a hemimodified DNA duplex that includes the target sequence, followed by a series of primer extension and strand displacement steps (e.g., U.S. Pat. No. 5,422,252 Walker et al.) Transcription-mediated or transcription-associated amplification reactions use a polymerase to make a complementary strand to the target in a double-stranded form that contains a functional promoter for a specific RNA polymerase that makes transcripts that can cycle isothermically to produce additional copies of transcripts that are detectable amplification products.

Transcription-mediated or transcription-associated amplification uses an RNA polymerase to produce multiple RNA transcripts from a nucleic acid template in isothermal reactions that use an RNA polymerase, a DNA polymerase, deoxyribonucleoside triphosphates, ribonucleoside triphosphates, and a promoter-primer, and optionally may include one or more additional oligonucleotides. These methods of amplification and reaction conditions have been described in detail previously (e.g., see U.S. Pat. Nos. 5,399,491 and 5,554,516 Kacian et al., U.S. Pat. No. 5,437,990 Burg et al., PCT Nos. WO 88/01302 and WO 88/10315 Gingeras et al., U.S. Pat. No. 5,130,238 Malek et al., U.S. Pat. Nos. 4,868,105 and 5,124,246 Urdea et al.).

Preferred embodiments of the present invention use transcription-mediated amplification (TMA, described in U.S. Pat. Nos. 5,399,491 and 5,554,516). It will, however, be apparent to one skilled in the art that the methods and oligonucleotide primer sequences described herein are readily applicable to use with any nucleic acid amplification method that synthetically extends primers by using a polymerase.

A detection probe is an oligomer that binds to a specific target sequence and, by binding, produces, directly or indirectly, a detectable signal that indicates the presence of the target sequence. A detection probe need not be labeled to produce a detectable signal, an example of such is an electrical impulse that results from the probe binding to the target. A labeled probe is made up of an oligomer that is linked, directly or indirectly, to a label. Methods of making and/or using labeled probes are well known (e.g., Sambrook et al., id., Chapt. 10; U.S. Pat. Nos. 6,361,945 Becker et al., 5,658,737 Nelson et al., 5,656,207 Woodhead et al., 5,547,842 Hogan et al., 5,283,174 Arnold et al., 4,581,333 Kourilsky et al., and 5,731,148 Becker et al.). Detection probes may include a synthetic linker (U.S. Pat. Nos. 5,585,481 and 5,639,604 Arnold et al.), and a chemiluminescent label, such as an acridinium ester (AE) compound (U.S. Pat. Nos. 5,185,439, 5,656,207, and 5,658,737).

A homogeneous detectable label is a label that can be detected in a homogeneous manner depending on whether the label is bound or unbound to a target. That is, detection of a label in a homogeneous reaction does not require physical separation of unbound forms of the label from the mixture in which the signal is detected. It will be appreciated by skilled artisans that a homogeneous reaction may occur in solution or on a support, e.g. on an array, biochip or gene chip. Homogeneous detectable labels and conditions for their detection are well known (e.g., U.S. Pat. Nos. 5,283,174, 5,656,207 and 5,658,737).

By “consisting essentially of” is meant that additional component(s), composition(s) or method step(s) that do not materially change the basic and novel characteristics of the present invention may be included in the compositions, kits, or methods of the present invention. Such characteristics include the ability to detect specifically the presence of HAV nucleic acid in a sample with a sensitivity of at least 80% for samples containing 25 to 30 copies of HAV per ml by using a combination of capture probe, amplification primers, and detection probe oligomers as described herein. Any component(s), composition(s), or method step(s) that have a material effect on the specificity and/or sensitivity of detection of HAV present in a sample by using the nucleic acid oligomers and in vitro methods described herein, would fall outside of this term.

Unless defined otherwise, all scientific and technical terms used herein have the same meaning as commonly understood by those skilled in the relevant art. Definitions of many of the terms used herein are provided in, e.g., Dictionary of Microbiology and Molecular Biology, 2nd ed. (Singleton et al., 1994, John Wiley & Sons, New York, N.Y.), The Encyclopedia of Molecular Biology (Kendrew, Ed., 1994, Blackwell Science Ltd., Cambridge, Mass.), or The Harper Collins Dictionary of Biology (Hale & Marham, 1991, Harper Perennial, New York, N.Y.). Unless mentioned otherwise, the techniques employed or contemplated herein are standard methodologies well known to one of ordinary skill in the art. Examples are included to illustrate some embodiments of the invention.

The present invention includes compositions (nucleic acid amplification oligomers, detection probes, and optionally capture oligomers) and methods for detecting HAV nucleic acid in a sample. To select sequences appropriate for use as the oligomers disclosed herein, known HAV genomic sequences (Beneduce, et al., 1995, Virus Res. 36 (2-3): 299-309, Fujiwara, et al., 2001, J. Hepatol. 35 (1): 112-119, Hu, et al., 2002, Acta Virol. 46 (3): 153-157), including those of different isolates, partial sequences, and complementary sequences available on a public database (e.g., GenBank accession nos. AB020564 to AB020569) were aligned by matching regions of the same or similar sequences and the aligned sequences were compared using well known techniques. Although sequence comparisons may be facilitated by use of algorithms, those skilled in the art can readily perform such comparisons manually and visually. Portions of HAV sequences that contain relatively few sequence variants between the compared sequences were chosen as a basis for designing synthetic oligomers suitable for use in the capture, amplification and detection steps described herein. Other well-known sequence characteristics, such as the GC content and the relative abundance of predicted secondary structures (e.g., hairpin turns or intramolecular pairing), were also considered in selecting the oligomer sequences.

Based on these analyses, regions of the HAV genome around nucleotides 200, 3700, 4700, 5700, 5800, 6000, and 7000 were chosen as potential target regions for detection of amplified HAV sequences. For each region, oligomers were designed for use in capturing the HAV RNA from a sample to purify it from other sample components, as amplification oligomers, and as probe sequences. Preferred embodiments of target regions are in portions of 0 to 305 nt, 4714 to 4765 nt, 5495 to 5788 nt, 5788 to 6069 nt, and 6952 to 7413 nt of the HAV genome.

Capture oligomer sequences generally include a sequence that binds specifically to a sequence near the target region to be amplified and a "tail" region used in attaching the hybridization complex that includes the target to a solid support, for example via hybridization to an immobilized oligomer (e.g., U.S. Pat. No. 6,110,678). Preferred capture oligomers include a target-specific sequence that binds specifically to a HAV RNA sequence and a covalently attached tail sequence (e.g., dT.sub.3dA.sub.30), as shown in SEQ ID NOS: 1 to 7. Those skilled in the art will understand that the target-specific portion of a capture oligomer (SEQ ID NOS: 8 to 14) or its RNA equivalent may be linked to any moiety that allows it to bind to an immobilized probe (e.g., a different tail sequence or a member of a binding pair, such as biotin or avidin). Any backbone may link the base sequence of a capture oligomer. Some embodiments use 2'-O-methyl linkages in the target-specific portion of a capture oligomer and standard DNA linkages in the tail portion. A polynucleotide tail sequence may be any sequence complementary to a sequence of an immobilized probe, and generally has a sequence length of about 5 to 50 residues, and is preferably a substantially homopolymeric sequence in a range of about 10 to about 40 residues (e.g., C.sub.10 to C.sub.40) that is complementary to an immobilized homopolymeric sequence (e.g., G.sub.15).

Primer sequences bind specifically to an HAV RNA target sequence or a complementary strand and flank a target sequence that is amplified, although primer sequences may contain additional sequences that do not bind to the target or its complementary sequence. A primer may be a promoter primer and include a 5' promoter sequence, such as a T7 RNA polymerase promoter (SEQ ID NO: 19). Embodiments of promoter primers include those of SEQ ID NOS: 20 to 49. Other embodiments of HAV-specific primers may include ancillary sequences, such as restriction endonuclease recognition sequences (SEQ ID NOS: 132 to 135). Those skilled in the art will appreciate that a target-specific sequence of a primer, with or without an attached promoter or ancillary sequence, may serve as a primer in a variety of in vitro amplification conditions. Amplification oligomers were designed for sequences in targeted regions of the HAV genome (e.g., around nucleotide positions 200, 3700, 4700, 5700, 5800, 6000, and 7000). Those skilled in the art will appreciate that these numbers refer to HAV target regions that are approximate only and that oligomers may function in an assay for more than one target region. That is, the identifying target region numbers provided here merely as a convenient shorthand reference for grouping preferred embodiments of the invention does not functionally restrict these oligomers. Amplification oligomers may be synthesized as DNA, RNA, complementary DNA or RNA sequences, or mixed DNA and RNA sequences, and may include one or more non-standard nucleic acid backbone linkages. For example, an oligomer of SEQ ID NO: 106 was synthesized with RNA bases and 2'-O-methyl linkages at residues 1 to 4 and standard DNA bases and linkages at the other residues.

For a first HAV target region (around position 200), amplification oligomers include those in a size range of about 23 to 26 nt that are contained in the sequence of SEQ ID NO: 138, and include at least the sequence of SEQ ID NO: 139 or SEQ ID NO: 140. Embodiments of such oligomers includes those of SEQ ID NO: 51 to SEQ ID NO: 57. Embodiments of promoter primers for this region, in a size range of about 50 to 53 nt, are those that include target-specific portions of SEQ ID NOS: 21 to 27. Amplification oligomers for this target region also include those in a size range of about 19 to 25 nt contained in SEQ ID NO: 141, and contain at least the sequence of any one of SEQ ID NOS: 142 to 146. Embodiments of amplification oligomers for this target region include those of SEQ ID NOS: 15 to 18, 20 to 27, 50 to 57, and 80 to 85.

For a second HAV target region (around position 3700), amplification oligomers include those in a size range of about 21 to 27 nt, contained in the sequence of SEQ ID NO: 60, or in SEQ ID NO: 86 and include at least SEQ ID NO: 156. Embodiments of promoter primers that include such target-specific portions for this region and are in a size range of about 48 to 54 nt include those of SEQ ID NOS: 29 to 32. Embodiments of amplification oligomers for this target region include those of SEQ ID NOS: 28 to 30, 58 to 60, and 86 to 88.

For a third HAV target region (around position 4700), amplification oligomers include those in a size range of about 24 to 30 nt that are contained in SEQ ID NO: 147 and include at least the sequence of SEQ ID NO: 148, or are contained in SEQ ID NO: 157 and include at least the sequence of SEQ ID NO: 158. Embodiments of amplification oligomers for this target region include those of SEQ ID NOS: 31, 32, 61, 62, 89, 90, and 91, of which SEQ ID NO: 31 and SEQ ID NO: 32 are promoter-primer embodiments that include a 5' promoter sequence attached to the target-specific sequence.

For a fourth HAV target region (around position 5700), amplification oligomers include those in a size range of about 18 to 27 nt that are contained in the sequence of SEQ ID NO: 93 or SEQ ID NO: 95. Embodiments of such oligomers include those that contain at least any one of SEQ ID NO: 97, SEQ ID NO: 159, and SEQ ID NO: 160. Embodiments of amplification oligomers for this target region include those of SEQ ID NOS: 33, 63, and 92 to 97, of which SEQ ID NO: 33 is a promoter primer embodiment that includes a 5' promoter sequence attached to the target-specific sequence.

For a fifth HAV target region (around position 5800), amplification oligomers include those in a size range of about 19 to 31 nt that are contained in SEQ ID NO: 149 and include at least the sequence of SEQ ID NO: 150. Embodiments of promoter primers, in a size range of about 51 to 56 nt, that include such target-specific portions are those of SEQ ID NOS: 34 to 40. Other embodiments of amplification oligomers for this target region include those of SEQ ID NOS: 64 to 70, and 97.

For a sixth HAV target region (around position 6000), amplification oligomers include those of about 24 to 28 nt contained in the sequence of SEQ ID NO: 161 and include the sequence of SEQ ID NO: 162. Embodiments of amplification oligomers for this target region include those of SEQ ID NOS: 41, 42, 71, 72, 98, 99, and 101, of which SEQ ID NOS: 41 and 42 are embodiments of promoter primers that include a 5' promoter sequence attached to the target-specific sequence.

For a seventh HAV target region (around position 7000), amplification oligomers include those in a size range of about 20 to 30 nt contained in SEQ ID NO: 151 and that include at least any one of the sequences of SEQ ID NO: 152 to SEQ ID NO: 155. Other embodiments of amplification oligomers for this target region are contained in SEQ ID NO: 163 and include at least the sequence of SEQ ID NO: 164. Additional embodiments are amplification oligomers that are contained in SEQ ID NO: 165 and include at least any one of the sequences of SEQ ID NOS: 166 to 168. Embodiments of promoter primers, in a size range of about 51 to 56 nt, that include HAV target-specific portions for this region are SEQ ID NOS: 43 to 49. Other embodiments of amplification oligomers for this region include those of SEQ ID NOS: 73 to 79, and 102 to 108.

Oligomers were designed to hybridize to and detect amplified HAV sequences, which include the detection probes of SEQ ID NOS: 109, 111, 113, 115, 117, 119, 121, 122, 123, 124, and 126 to 130. Those skilled in the art will appreciate that a detection probe will be chosen to hybridize to a sequence contained within an amplified sequence that is determined by the combination of amplification oligomers that are used. Detection probe oligomers may be synthesized as DNA, RNA, or mixed DNA and RNA polymers, and may include alternative backbone linkages such as 2'-O-methyl linkages. For example, oligomers of SEQ ID NOS: 109, 111, 117, 119, 121, 122, 128, and 130 were synthesized with 2'-0-methyl linkages, and oligomers of SEQ ID NOS: 124 and 127 were synthesized as mixed DNA and RNA nucleotides with 2'-O-methyl linkages from the second residue to the 3' terminal residue. Preferred embodiments of detection probes have an attached chemiluminescent label, preferably an acridinium ester (AE) compound (U.S. Pat. Nos. 5,185,439, 5,639,604, 5,585,481, and 5,656,744), which in preferred embodiments are attached to the probe by a non-nucleotide linker (see U.S. Pat. Nos. 5,585,481, 5,656,744, and 5,639,604, particularly at column 10, line 6 to column 11, line 3, and Example 8). Embodiments of the probe oligomers were labeled by using known methods with an AE compound between residues 9 and 10 for SEQ ID NOS: 119, 121 and 124, between residues 10 and 11 for SEQ ID NOS: 115, 117, 126, 127 and 128, between residues 11 and 12 for SEQ ID NOS: 109, 111, 123, 124 and 130, between residues 12 and 13 for SEQ ID NOS: 113, 122 and 129, and between residues 13 and 14 for SEQ ID NO: 122. Probe oligomers were tested and characterized by hybridization with complementary oligomer sequences, by using standard methods for determining Tm and/or differential hydrolysis of the acridinium ester in a hybridization complex (described in detail in U.S. Pat. No. 5,283,174). For example, hybridizations were performed by using complementary pairs of sequences of SEQ ID NO: 109 and SEQ ID NO: 110, SEQ ID NO: 111 and SEQ ID NO: 112, SEQ ID NO: 113 and SEQ ID NO: 114, SEQ ID NO: 115 and SEQ ID NO: 116, SEQ ID NO: 117 and SEQ ID NO: 118, SEQ ID NO: 119 and SEQ ID NO: 120, SEQ ID NO: 124 and SEQ ID NO: 125, SEQ ID NO: 128 and SEQ ID NO: 100, and SEQ ID NO: 130 and SEQ ID NO: 131. Hybridization testing may be performed by using other complementary sequences, such as SEQ ID NO: 124 with SEQ ID NO: 137, and SEQ ID NO: 129 with SEQ ID NO: 136.

Compositions of the present invention include kits for detecting HAV nucleic acid sequences. Such kits include amplification oligomers as disclosed herein that function as primers for amplifying HAV nucleic acid sequences in vitro. Exemplary kits include a first amplification oligomer that hybridizes specifically to a sequence in a target region of the HAV RNA genome or its complementary sequence, and a second amplification oligomer that hybridizes specifically to another HAV sequence in the target region, preferably one complementary to the HAV RNA genomic sequence. Embodiments of kits include amplification oligomers that are combinations of primers and promoter primers as described herein. Kits may also contain one or more oligomers that serve as detection probes for detecting amplified HAV sequences of the target region of the primers selected for the kit. Embodiments of kits that include of probe oligomers use one or more of the detection probe sequences as described herein, which may include a label attached directly or indirectly to the probe oligomer. Kits may also contain oligomers that serve as capture oligomers for purifying a target HAV RNA from a sample. Embodiments of such capture oligomers as described herein may contain a covalently attached tail sequence or other binding moiety used in target capture. Kits useful for practicing the methods described herein are also included in the invention, and preferred embodiments include at least two amplification oligomers as described herein, and may also include reagents for performing in vitro amplification, e.g., enzymes, salt solutions, and nucleic acid synthesis substrate compounds. Oligomers described herein may be packaged in a variety of different embodiments, and thus, those skilled in the art will appreciate that the invention embraces many different kit configurations. For example, a kit may include amplification oligomers for only one target region of the HAV genome, or it may include amplification oligomers for multiple HAV target regions. Those skilled in the art will appreciate that a kit that includes a detection probe will include a probe that binds to a sequence amplified by the amplification oligomers of the kit. That is, selection of amplification oligomers and detection probe oligomers for a kit will be linked by their intended target region.

An embodiment of the assay to detect HAV nucleic acid in a sample includes the steps of capturing the HAV target nucleic acid from a sample by using a capture oligomer, amplifying a region of the captured HAV nucleic acid by using a combination of at least two primers, and detecting the amplified HAV sequence by specifically hybridizing it with a detection probe oligomer and detecting a signal that results from the probe bound to the amplified HAV sequence. Preferred embodiments use a transcription-associated or transcription-mediated amplification reaction. Either the amplified nucleic acid or the probe may be labeled, or both may be unlabeled and a detectable signal results from an indirect label or response associated with the hybridization complex, such as an electrical impulse resulting from hybridization of the probe and the amplified nucleic acid.

The capturing step preferably uses a capture oligomer that includes a target-specific sequence (e.g., SEQ ID NOS: 8 to 14) that specifically hybridizes to a HAV target sequence and a moiety that permits the hybridized target nucleic acid to be separated from other sample components. The capturing step may use a capture oligomer that also includes a tail portion, e.g. as in SEQ ID NOS: 1 to 7, that serve as the moiety that allows the target nucleic acid to be separated from other sample components by hybridization of the tail portion to an immobilized probe, as previously described (U.S. Pat. No. 6,110,678). Preferred embodiments use supports that are magnetic spheres that are monodisperse (i.e., uniform in size±about 5%) with covalently attached or immobilized poly-dT oligomers that hybridize to a complementary tail sequence of the capture oligomer. The hybridization complex that includes at least the target nucleic acid and the capture oligomer, and preferably also includes the immobilized probe, is separated from the other sample components by using standard physical separation methods (e.g., application of magnetic force, filtration, or centrifugation) and the captured target nucleic acid may be washed one or more times to further purify the target nucleic acid from other sample components. For example, particles with the attached target nucleic acid in a hybridization complex are suspended one or more times in a washing solution that maintains the complex and then the particles with the attached complex are retrieved from the washing solution as described above.

Amplifying the captured HAV target sequence uses an in vitro amplification reaction that uses at least two primers that flank the sequence to be amplified, e.g., an HAV sequence flanked by SEQ ID NO: 66 and SEQ ID NO: 95, or their complementary sequences. One embodiment uses a transcription-associated amplification reaction that makes many RNA copies of a sequence in substantially isothermal conditions (as described previously in U.S. Pat. Nos. 5,399,491 and 5,554,516). Transcription-associated amplification uses two types of primers (one a promoter primer that contains a promoter sequence for an RNA polymerase), enzymes (a reverse transcriptase and an RNA polymerase), substrates (deoxyribonucleoside triphosphates, ribonucleoside triphosphates) and appropriate salts and buffers in solution to produce multiple RNA transcripts from a nucleic acid template. Briefly, a promoter primer hybridizes specifically to a target RNA sequence and reverse transcriptase creates a first strand cDNA by extension from the 3' end of the promoter primer and degrades the template strand in the resulting DNA:RNA duplex by using RNase H activity. A second primer binds to the cDNA and another DNA strand is synthesized by the reverse transcriptase from the end of the second primer, to create a double-stranded DNA with a functional promoter sequence to which the RNA polymerase binds. Multiple RNA transcripts ("amplicons") are transcribed and each can be a template in a new round of replication as described above, thus generating large amounts of single-stranded amplified sequence (e.g., about 100 to 3,000 transcripts from a single template). Embodiments of the invention that use a transcription-associated amplification reaction may use promoter primers (SEQ ID NOS: 20 to 49) with other primers (SEQ ID NOS: 15 to 18, 80 to 99, and 101 to 108) to amplify selected HAV sequences for detection.

The detecting step uses at least one probe that binds specifically to the amplified HAV sequences. Embodiments may use any know detection method (e.g., detection of a radioactive, fluorescent, enzymatic, colorimetric, electrical, or luminescent signal) to detect binding of the detection probe to the amplified HAV sequences, and the detected signal indicates the presence of HAV in the sample. Embodiments of probe oligomers (SEQ ID NOS: 109, 111, 113, 115, 117, 119, 121, 122 to 124, 126 to 130) may be unlabeled or labeled using any of a variety of known labels. In preferred embodiments, the detection step is performed in a homogeneous detection reaction without removing the unbound detection probe from the mixture. Embodiments of the probe oligomers for use in homogeneous detection reactions are preferably labeled with one of a variety of AE compounds, which produce a chemiluminescent signal that is detected as described in detail previously (U.S. Pat. Nos. 5,283,174, 5,656,744, and 5,658,737).

A preferred assay embodiment generally includes the following steps. A HAV-containing sample is provided, which may be prepared by using standard laboratory methods to make a substantially aqueous solution or suspension that contains HAV. An aliquot (0.5 ml) of the sample solution or suspension is mixed with about an equal volume (0.4 to 0.5 ml) of a target capture reagent, i.e., a solution that contains one or more capture oligomers (4 pmol/reaction), magnetic particles with attached immobilized probes complementary to a portion of the capture oligomers, and salt compounds to provide a hybridization condition. The target capture reagent preferably includes a detergent or other chaotropic agent that disrupts the HAV particles and releases HAV RNA for hybridization with capture oligomers. The mixture is incubated 20-30 min at 60. deg.C to allow hybridization of the target-specific portion of the capture oligomer to the HAV target sequence and then at room temperature for 20-30 min to allow binding of the capture oligomer and immobilized probe. A magnetic field is applied to the outside of the reaction container for about 10 min to separate the particles with the attached hybridization complexes that include HAV RNA, and the solution phase containing other sample components is aspirated away. To wash the particles with attached hybridization complexes, they are suspended in 1 ml of a wash buffer, separated from the solution substantially as described above, and the solution is removed. Particles with attached hybridization complexes that include the purified HAV RNA are mixed with a solution that contains amplification reagents (buffers, salts, dXTP and XTP substrates), and a combination of amplification oligomers (a promoter primer and a primer combination, each at 3 to 30 pmol, generally 15 pmol each), and covered with oil (0.2 ml of filtered silicon oil) to prevent evaporation, and incubated for 10 min at 60. deg.C, then for 10 min at 42. deg.C, and then enzymes are added (reverse transcriptase and RNA polymerase), and the mixture is incubated for 60 min at 42. deg.C. For detection, the amplification reaction mixture is incubated with at least one acridinium labeled detection probe oligomer to provide a maximum detectable signal (relative light units or RLU) of 2 million or less, as detected by using standard methods on a luminometer (e.g., Gen-Probe Leader®, Gen-Probe Incorporated, San Diego, Calif.). Detection probe is mixed with undiluted or a diluted aliquot of the amplification reaction mixture in a hybridization solution, incubated for 20 min at 60. deg.C to allow hybridization of the probe oligomer to the amplified target sequence. Then, label on unbound probes is hydrolyzed by using a selection reagent (e.g., a base) and incubated for 10 min at 60.deg.C, followed by adding a detection reagent (e.g., H.sub.2O.sub.2) to produce chemiluminescence, followed by pH neutralization (e.g., by adding acid), and detecting the chemiluminescent signal (RLU) on a luminometer (e.g., 1-5 sec).

For use in the methods described above, capture oligomers, amplification oligomers and detection probes may be synthesized using standard methods to produce DNA, RNA, or mixed DNA and RNA polymers. Such oligomers may include standard or modified linkages and/or naturally occurring nucleosides (A, T or U, G, C), analogs (e.g., inosine), or synthetic purine and pyrimidine derivatives (e.g., P or K bases) (Lin & Brown, 1989, Nucl. Acids Res. 17:10373-83; Lin & Brown, 1992, Nucl. Acids Res. 20: 5149-52).

The general principles of the present invention may be more fully appreciated by reference to the following examples describe some embodiments of the present invention. In addition to the specific components described in the examples, generally the following reagents were used in the experiments described below. Target capture reagent was made up of 790 mM HEPES, 680 mM LiOH, 10% (v/v) lithium lauryl sulfate (LLS), 230 mM succinic acid, 0.03% (v/v) anti-foaming agent, 100.micro.g/ml magnetic particles (1 micron SERA-MAG.sup™ particles, Seradyn, Inc. Indianapolis, Ind.) with covalently attached poly-dT.sub.14, and one or more capture oligomers, each at 4 pmol per 400.micro.1. Wash buffer was made up of 150 mM NaCl, 10 mM HEPES, 6.5 mM NaOH, 1 mM EDTA, 0.3% (v/v) ethanol, 0.1% SDS, 0.02% (w/v) methyl paraben, 0.01% (w/v) propyl paraben, at pH 7.5. Amplification reagent was made up of 11.6 mM Tris base, 15 mM Tris-HCl, 22.7 mM MgCl.sub.2, 23.3 mM KCl, 3.33% glycerol, 0.05 mM Zn-acetate, 0.665 mM dATP, 0.665 mM dCTP, 0.665 mM dGTP, 0.665 mM dTTP, 5.32 mM ATP, 5.32 mM CTP, 5.32 mM GTP, and 5.32 mM UTP, at pH 7. Enzyme reagent was made up of 140 U/.micro.1. T7 RNA polymerase, 224 RTU/.micro.1. of Moloney Murine Leukemia Virus reverse transcriptase (MMLV-RT), 16 mM HEPES, 70 mM N-acetyl-L-cysteine, 3 mM EDTA, 0.05% (w/v) Na-azide, 20 mM Tris, 50 mM KCl, 20% (v/v) glycerol, 10% (v/v) TRITON® X-102, 150 mM trehalose, at pH 7. (Enzyme units typically are 1 U of T7 RNA polymerase incorporates 1 nmol of ATP into RNA in 1 hr at 37.deg.C using a DNA template containing a T7 promoter, and 1 U of MMLV-RT incorporates 1 nmol of dTTP in 10 min at 37.deg.C using 200-400.micro.M oligo-dT primer and poly-A template.) Probe reagent was made up of 100 mM succinic acid, 2% (w/v) LLS, 230 mM LiOH, 15 mM Aldrithiol-2, 1.2 M LiCl, 20 mM EDTA, 20 mM EGTA, 3% (v/v) ethanol, adjusted to pH 4.7 with LiOH. Selection reagent was made up of 600 mM boric acid, 182 mM NaOH, 1% (v/v) octoxynol (TRITON® X-100), at pH 8.5. Detection reagents were Detect Reagent I, which contained 1 mM nitric acid and 32 mM H.sub.2O.sub.2, and Detect Reagent II (to neutralize pH), which was 1.5 M NaOH (see U.S. Pat. No. 5,283,174 for details).

EXAMPLE 1

Detection Probe Characterization

Oligomers of SEQ ID NOS: 109, 111, 113, 119, 123, 126, and 130 were synthesized using standard phosphoramidite chemistry (Caruthers et al., 1987, Methods in Enzymol., 154: 287) and an acridinium ester (AE) label was attached via a linker by using well-known methods (U.S. Pat. Nos. 5,185, 439 and 5,283,174), and probes were purified by using routine chromatographic methods (e.g., HPLC). Probes were AE labeled between residues 11 and 12 for SEQ ID NO: 109, SEQ ID NO: 111, SEQ ID NO: 123, and SEQ ID NO: 130, between residues 12 and 13 for SEQ ID NO: 113, between residues 10 and 11 for SEQ ID NO: 126, and between residues 9 and 10 for SEQ ID NO: 119. To characterize the probe oligomers, each was hybridized with a complementary DNA and/or RNA oligomer (e.g., SEQ ID NO: 109 with SEQ ID NO: 110, SEQ ID NO: 111 with SEQ ID NO: 112, SEQ ID NO: 113 with SEQ ID NO: 114, SEQ ID NO: 119 with SEQ ID NO: 120, and SEQ ID NO: 130 with SEQ ID NO: 131), at temperatures below the predicted Tm of the probe, and then the Tm was experimentally determined by using standard methods. The differential hydrolysis of the AE label in probes hybridized to a complementary oligomer compared to AE in unbound probe was also experimentally determined by using standard methods (see U.S. Pat. No. 5,283,174). Briefly, the ratio of the time required for half of the signal to be lost due to AE hydrolysis in the hybrid compared to the time required for hydrolysis of half of the label in unbound probe was determined The Tm's were in the range of 59.deg.C to 66.deg.C for oligomers of SEQ ID NOS: 109, 111, 113, 119 and 130 when hybridized to a complementary DNA, and Tm's were in the range of 76.deg.C to 81.deg.C for oligomers of SEQ ID NOS: 109, 111, 123, 126 and 130 when hybridized to a complementary RNA. The differential hydrolysis ratios were in the range of 12 to 25 for probes of SEQ ID NOS: 109, 111, 113, 119 and 130 when hybridized to complementary DNA, and the differential hydrolysis ratios were in the range of 18 to 104 for probes of SEQ ID NOS: 109, 111, 123, 126 and 130 when hybridized to complementary RNA. Separately, similar hybridization and differential hydrolysis tests were performed for probes of SEQ ID NO: 121 labeled between residues 9 and 10, SEQ ID NO: 122 labeled between residues 13 and 14, SEQ ID NO: 124 labeled between residues 9 and 10, and SEQ ID NO: 130 labeled between residues 11 and 12, and the differential hydrolysis ratios were in the range of 43 to 190 when the probes were hybridized to complementary RNA. These results showed that all of these synthetic probe oligomers hybridized specifically to their complementary target sequences and produced detectable signals useful for specifically detecting amplified HAV sequences.

EXAMPLE 2

Purification of HAV RNA from Samples

Capture oligomers of SEQ ID NOS: 1 to 7, synthesized by using standard phosphoramidite chemistry and purified using standard methods, were tested for their ability to capture HAV RNA released from virus in human plasma samples. Samples were made by adding HAV particles at known concentrations to normal human plasma (0.5 ml) and the samples containing HAV (e.g., 500 to 1000 per reaction) were mixed with an equal volume of the target capture reagent containing each capture oligomer individually (4 pmol/reaction) and polydT-magnetic particles. The mixtures were incubated for 30 min at 60.deg.C, and then for 30 min at room temperature to form hybridization complexes that capture HAV RNA to the particles. The magnetic particles with attached captured HAV RNA were separated by applying a magnetic field for 10 min to the outside of the container, then the solution phase was aspirated away to remove other sample components, and the particles with attached hybridization complexes were washed twice sequentially, each using 1 ml of the wash buffer at room temperature and aspirating the washing solution away from the particles. Particles with attached hybridization complexes were then suspended in probe reagent (0.1 ml) containing a labeled detection probe, as described in Example 1, and incubated for 20 min at 60.deg.C, followed by addition of selection reagent (0.2 ml), mixing and incubation for 10 min at 60.deg.C. Production and detection of the chemiluminescent signal was performed by adding 200.micro.1 of a detect reagent I, incubation, and pH neutralization of the mixture by adding 200.micro.1 of detect reagent II, and measuring RLU by using a luminometer, substantially as described above. For all of the capture oligomers tested, the presence of the HAV RNA in the sample was detected by detecting a positive signal significantly higher than background (RLU for a similar sample that contained no HAV). The assays showed little significant performance differences between the capture oligomers.

EXAMPLE 3

Amplification and Detection of HAV Sequences

HAV samples in normal human plasma were prepared substantially as described in Example 2 and the HAV RNA was captured by using various combinations of capture oligomers for assays to amplify and detect selected target regions of the HAV genome. For a target region of 0-305 residues of the genome, SEQ ID NOS: 2, 3, and 4 were used in the capture step. For a target region of 4714-4765 residues of the genome, SEQ ID NOS: 4, 5, 6, and 7 were used in the capture step. For a target region of 5495-5788 residues of the genome, SEQ ID NOS: 1 and 6 were used in the capture step. For a target region of 5788-6069 residues of the genome, SEQ ID NO: 2 was used in the capture step. For a target region of 6952-7413 residues of the genome, SEQ ID NOS: 1, 4, 5 and 7 were used in the capture step. The capture steps were performed substantially as described in Example 2.

The captured HAV RNA was amplified in reactions substantially as described above that contained different combinations of amplification oligomers to serve as primers for different target regions in the HAV genome. The primers used to amplify the target regions were as follows: SEQ ID NO: 16 and SEQ ID NO: 22 for the 0-305 residues region, SEQ ID NO: 89 and SEQ ID NO: 32 for the 4714-4765 residues region, SEQ ID NO: 92 and SEQ ID NO: 33 for the 5495-5788 residues region, SEQ ID NO: 94 and SEQ ID NO: 37 for the 5788-6069 residues region, and SEQ ID NO: 108 and SEQ ID NO: 46 for the 6952-7413 residues region. The amplification reactions were all performed substantially the same as described above. That is, particles with the attached HAV RNA from the target capture step were mixed with amplification reagent and the individual combination of amplification oligomers described above (generally 15 pmol each), and covered with silicon oil (0.2 ml) to prevent evaporation, and incubated for 10 min at 60.deg.C and then for 10 min at 42.deg.C. The enzyme reagent was added (reverse transcriptase and RNA polymerase), and the amplification reactions were incubated for 60 min at 42.deg.C.

For detection, the amplification mixture was incubated with a labeled detection probe oligomer that hybridizes specifically to sequences contained in the amplified region. These included SEQ ID NO: 109 or SEQ ID NO: 111 for the 0-305 residues region, SEQ ID NO: 115 for the 4714-4765 residues region, SEQ ID NO: 117 for the 5495-5788 residues region, SEQ ID NO: 121 and/or SEQ ID NO: 122 for the 5788-6069 residues region, and SEQ ID NO: 129 or SEQ ID NO: 130 for the 6952-7413 residues region. The probes were provided in the probe reagent in an amount previously determined based on the specific activity of the labeled probe to produce a maximum detectable signal of 2 million RLU or less from the hybridized labeled probe. The probes and amplified sequences were incubated in the probe reagent at 55-60.deg.C, and the chemiluminescent signal was produced from hybridized probes and detected substantially as describe in Examples 1 and 2. For all of the primer combinations tested with the captured HAV RNA, the sensitivity of the amplification assay detected between 400 and 1000 copies of HAV RNA present in the samples.

The various combinations of capture oligomers, amplification oligomers and detection probes used for amplification and detection of selected HAV target regions in these tests are summarized in Table 1.

TABLE 1

Combinations of Oligomers for Testing for HAV in Samples

| Target Region (Residues) | Capture Oligomer(s) | Amplification Oligomers | Detection Probe(s) |
|---|---|---|---|
| 0-305 | SEQ ID NOS: 2, 3 and 4 | SEQ ID NOS: 16 and 22 | SEQ ID NO: 109 or 111 |
| 4714-4765 | SEQ ID NOS: 4, 5, 6 and 7 | SEQ ID NOS: 32 and 89 | SEQ ID NO: 115 |
| 5495-5788 | SEQ ID NOS: 1 and 6 | SEQ ID NOS: 33 and 92 | SEQ ID NO: 117 |
| 5788-6069 | SEQ ID NO: 2 | SEQ ID NOS: 37 and 94 | SEQ ID NOS: 121 and/or 122 |
| 6952-7413 | SEQ ID NOS: 1, 4, 5 and 7 | SEQ ID NOS: 46 and 108 | SEQ ID NO: 129 or 130 |

Similar experiments were performed using the different capture oligomers (SEQ ID NOS: 1, 2, 3, 4, 5, 6, and 7) separately with HAV-containing samples, in which the target capture step was performed substantially as described above on nine replicates for each assay condition. For all of these tests the target region was residues 5788 to 6069 of HAV, for which the same amplification oligomers of SEQ ID NO: 36 and SEQ ID NO: 96 were used in the amplification reactions with the captured HAV RNA performed as described above, and amplified products were detected by measuring chemiluminescence from hybridized detection probe (SEQ ID NO: 123 or 124, labeled with AE between residues 11 and 12) as described above. The results of these assays are shown in Table 2 (average RLU for nine replicates).

TABLE 2

Amplification and Detection of the 5788-6069 residue Target Region

| Purification by Capture Oligomer | Detected Signal (mean RLU) |
|---|---|
| SEQ ID NO: 1 | 292,136 |
| SEQ ID NO: 2 | 275,732 |
| SEQ ID NO: 3 | 478,463 |
| SEQ ID NO: 4 | 522,837 |
| SEQ ID NO: 5 | 443,830 |
| SEQ ID NO: 6 | 416,905 |
| SEQ ID NO: 7 | 369,337 |

These results show that all of the capture oligomers sufficiently purified HAV RNA from samples to be amplified and detected to indicate the presence of HAV in the samples.

EXAMPLE 4

Detection of HAV in Plasma Samples

This example uses an assay that detected HAV nucleic acid in HAV-positive plasma samples. To prepare samples, a commercially available stock of HAV in human plasma was diluted into HAV-negative plasma to obtain samples with a titer of 25, 30, 100, 300 and 500 copies/ml; a negative control was plasma with no HAV. For each assay, performed using 20 replicate samples per assay, 0.5 ml samples were mixed with 0.4 ml of target capture reagent containing capture oligomers of SEQ ID NO: 4 (6.5 pmol/reaction) and SEQ ID NO: 5 (1.3 pmol/reaction) and the target capture step was performed substantially as described in Example 3, except that the 60.deg.C incubation was for 20 min. For each assay, the washed magnetic particles with the attached hybridization complexes that included capture oligomers of SEQ ID NOS: 4 and 5 bound to HAV RNA were then used in the amplification reactions that contained 75.micro.1 of amplification reagent containing amplification oligomers of SEQ ID NO: 36 (13 pmol/reaction) and SEQ ID NO: 96 (20 pmol/reaction). As described above, the mixture was covered with an oil layer, incubated 10 min at 60.deg.C, the enzyme reagent (25.micro.1) was added, and the mixture was incubated for 60 min at 41.5.deg.C to allow amplification of the HAV target sequence. The amplified sequences were detected by using 2-methyl-AE-labeled detection oligomers of SEQ ID NOS: 121 and 122 (0.007-0.13 pmol/reaction of each in 25.micro.1 volume of probe reagent) which were incubated for 15 min at 60.deg.C for hybridization of the probes to the amplified HAV sequences, and then 250.micro.1 of selection reagent was added and the mixture was incubated 10 min at 60.deg.C to hydrolyze AE in unbound probes, and detection was performed as described above using the Detect Reagents I and II to produce the chemiluminescent signal (RLU) measured in a luminometer (LEADER.sup™ HC Plus, Gen-Probe Inc., San Diego, Calif.). The results showed that the assay has a sensitivity of about 80% to 100% for samples containing 25 copies of HAV per ml, about 90% to 100% for samples containing 30 copies of HAV per ml, about 98% to 100% for samples containing 100 copies of HAV per ml, and 100% for samples containing 300 and 500 copies of HAV per ml. No positive results were detected for the negative control (samples containing 0 copies of HAV). These results show that the assay detects HAV in clinical samples with a sensitivity of about 25 copies of HAV per ml of sample.

EXAMPLE 5

Detection of HAV RNA and Another Viral Target in the Same Sample

This example describes an assay that includes the steps of target capture, amplification and detection substantially as described in Examples 1 to 4 to detect HAV and similar steps using additional oligomers to capture, amplify and detect another target, human parvovirus B19, in the same sample. To detect HAV, the capture oligomers are of SEQ ID NOS: 4 and 5, the amplification oligomers are of SEQ ID NOS: 36 and 96, and the detection probes are of SEQ ID NOS: 121 and 122, substantially as described in Example 4. To detect parvovirus B19 nucleic acid, the capture probe is of SEQ ID NO: 169, the amplification oligomers are of SEQ ID NOS: 170 and 171, and the detection probes are of SEQ ID NO: 173 labeled between residues 5 and 6 and SEQ ID NO: 174 labeled between residues 9 and 10. The assay to detect parvovirus B19 is similar to a previously described assay (U.S. Pat. Pub. No. US-2003-0124578-A1). Samples of 0.5 ml normal human plasma are prepared to contain known amounts of HAV and parvovirus B 19, and then mixed with 0.4 ml of target capture reagent containing all of the capture oligomers described above. Target capture is performed substantially as described in Example 2. The purified HAV and parvovirus B19 targets are amplified in the same amplification reaction mixture, substantially as described in Examples 3 and 4, but using the combination of HAV-specific and parvovirus-specific amplification oligomers described above. Following amplification of the HAV target sequence and the parvovirus B 19 target sequence, the detection step uses the HAV-specific probes and parvovirus-specific probes as described above, but where the probes for the different target viruses are each labeled with a different acridinium ester compound to allow detection of different signals in the detection reaction by using differential kinetics (as described previously, see U.S. Pat. No. 5,658,737). In these assays, both the HAV and the parvovirus B 19 nucleic acid are detected in the samples that contain both targets. The sensitivity of the assay for detection of HAV is about 25 copies/ml, i.e., positive signals are detected for 80% to 100% of the samples containing 25, 30, 100, 300 and 500 copies/ml of HAV. The sensitivity of the assay for detection of parvovirus B19 in the sample is as low as 150 international units/ml (IU/ml), i.e., positive signals are detected for 20% to 40% of samples containing 150 IU/ml. The assay reliably detects 400 or more parvovirus B19 IU/ml, i.e., 70% to 100% positive detection for samples containing 400, 600, 800, 1600 and 3000 IU/ml. These results show that HAV nucleic acid is specifically detected when the sample includes HAV and another virus, human parvovirus B 19, which is also specifically detected.

We claim:

1. A combination of at least two oligomers for amplifying a HAV target region comprising:

a first amplification oligomer that is a length of 23 to 26 contiguous nucleotides contained in the sequence of SEQ ID NO:138 that includes at least the sequence of SEQ ID NO:139 or SEQ ID NO:140, and a second amplification oligomer that is a length of 19 to 25 contiguous nucleotides in contained in the sequence of SEQ ID NO:141 and that includes at least one sequence of SEQ ID NOS: 142 to 146.

2. The combination of at least two oligomers of claim 1, wherein the first amplification oligomer is selected from the group consisting of: SEQ ID NO:51, SEQ ID NO:52, SEQ ID NO:53, SEQ ID NO:54, SEQ ID NO:55, and SEQ ID NO:56 and wherein the second amplification oligomer is 19 to 25 nt in length and is contained in the sequence of SEQ ID NO: 141 and contains at least one sequence of SEQ ID NOS: 142 to 146.

3. The combination of at least two oligomers of claim 1, further comprising at least one capture probe oligomer selected from the group consisting of SEQ ID NOS: 1 to 7 and SEQ ID NOS: 8-14 linked to a moiety that allows it to bind a solid support.

4. The combination of at least two oligomers of claim 1, further comprising at least one detection probe oligomer selected from the group consisting of SEQ ID NO:109, and SEQ ID NO:111.

5. The combination of at least two oligomers according to claim 1, wherein said combination is packaged in a kit.

6. A method of detecting the presence of HAV in a sample comprising the steps of:

purifying HAV nucleic acid from other components in a sample containing HAV;

amplifying a HAV target sequence in the purified HAV nucleic acid, or a cDNA made therefrom, by using an in vitro amplification reaction that includes at least two amplification oligomers specific for a selected HAV target region, which include:

for a first HAV target region, a first amplification oligomer that is a length of about 23 to 26 contiguous nucleotides contained in the sequence of SEQ ID NO:138 and that includes at least the sequence of SEQ ID NO:139 or SEQ ID NO:140; and a second amplification oligomer that is a length of 19 to 25 contiguous nucleotides contained in the sequence of SEQ ID NO:141 and that includes at least one sequence of SEQ ID NOS: 142 to 146;

to produce an amplified product of the selected HAV target region; and detecting the amplified product.

7. The method of claim 6, wherein the purifying step contacts the sample with at least one capture probe oligomer selected from the group consisting of SEQ ID NOS: 1 to 7 and SEQ ID NOS: 8-14 linked to a moiety that allows it to bind a solid support, wherein a target hybridization sequence of said at least one capture probe oligomer hybridizes specifically to a sequence in HAV RNA to form a hybridization complex with the HAV RNA, and can be used with a solid support to separate the HAV RNA from other sample components.

8. The method of claim 6, wherein the amplifying step amplifies a sequence in the first HAV target region by using at least two oligomers specific for the first HAV target region selected from the group consisting of: SEQ ID NO:51, SEQ ID NO:52, SEQ ID NO:53, SEQ ID NO:54, SEQ ID NO:55, and SEQ ID NO:56; and wherein the detecting step uses at least one detection probe that hybridizes specifically to the amplified product of the first HAV target region.

9. The method of claim 6, wherein said detecting step uses a nucleic acid detection oligomer, wherein said nucleic acid detection oligomer comprises a target hybridizing sequence that specifically hybridizes with at least one amplified product generated in said amplifying step.

10. The method of claim 9, wherein said nucleic acid detection oligomer comprises a target hybridizing region nucleic acid sequence consisting essentially of a nucleic acid sequence selected from the group consisting of SEQ ID NO:109 and SEQ ID NO:111.

11. The method of claim 9, wherein said nucleic acid detection oligomer further comprises a 2'-O-methyl linkages, a chemiluminescent label, an acridinium ester label, a synthetic linker or combinations thereof.

12. The method of claim 6, wherein the first amplification oligomer further comprises a promoter sequence joined at its 5' end, and wherein the promoter sequence is SEQ ID NO:19.

13. The method of claim 12, wherein the first amplification oligomer is selected from the group consisting of SEQ ID NOS: 21-26, and wherein the second amplification oligomer is selected from the group consisting of SEQ ID NOS: 15 to 18 and 80 to 85.

14. The method of claim 6, wherein the first amplification oligomer is SEQ ID NO:52 further comprising SEQ ID NO:19 joined to its 5' end, the second amplification oligomer is SEQ ID NO:16 and amplified product is detected using detection probes that are SEQ ID NO:109, SEQ ID NO:111 or both.

15. The method of claim 6, wherein the sample is a biological sample collected from humans.

16. The method of claim 15, wherein the sample collected from a human is a plasma sample.

17. The method of claim 15, wherein the sample collected from a human is a sample used for the preparation of therapeutic factors isolated from humans.

18. The method of claim 14, wherein the sample collected from a human is a sample used for the preparation of therapeutic factors isolated from humans.

19. The method of claim 6, further comprising detecting the presence of parvovirus B19 in the sample.

20. The method of claim 14, further comprising detecting the presence of parvovirus B19 in the sample.

* * * * *